(12) United States Patent
Bhuiyan et al.

(10) Patent No.: US 11,416,987 B2
(45) Date of Patent: Aug. 16, 2022

(54) IMAGE BASED SCREENING SYSTEM FOR PREDICTION OF INDIVIDUAL AT RISK OF LATE AGE-RELATED MACULAR DEGENERATION (AMD)

(71) Applicant: iHealthScreen Inc., Flushing, NY (US)

(72) Inventors: Mohammed Alauddin Bhuiyan, Queens Village, NY (US); Md. Akter Hussain, Kingsville (AU); Arun Govindaiah, Flushing, NY (US)

(73) Assignee: IHEALTHSCREEN INC., Flushing, NY (US)

( * ) Notice: Subject to any disclaimer, the term of this patent is extended or adjusted under 35 U.S.C. 154(b) by 19 days.

(21) Appl. No.: 16/847,019

(22) Filed: Apr. 13, 2020

(65) Prior Publication Data

US 2020/0242763 A1 Jul. 30, 2020

Related U.S. Application Data

(63) Continuation of application No. PCT/US2018/032697, filed on May 15, 2018.

(60) Provisional application No. 62/572,292, filed on Oct. 13, 2017.

(51) Int. Cl.
*G06T 7/00* (2017.01)
*G06T 7/38* (2017.01)
(Continued)

(52) U.S. Cl.
CPC .......... *G06T 7/0012* (2013.01); *A61B 5/7267* (2013.01); *A61B 5/7275* (2013.01); *G06T 7/11* (2017.01); *G06T 7/12* (2017.01); *G06T 7/38* (2017.01); *G16H 40/67* (2018.01); *G16H 50/20* (2018.01); *A61B 3/12* (2013.01); *G06T 2207/20032* (2013.01); *G06T 2207/20072* (2013.01); *G06T 2207/20081* (2013.01); *G06T 2207/20084* (2013.01); *G06T 2207/30041* (2013.01); *G16H 50/30* (2018.01)

(58) Field of Classification Search
CPC .......... G06T 7/0012; G06T 7/38; G06T 7/11; G06T 2207/20032; G06T 2207/20081; G06T 2207/20084; G06T 2207/30041; G06T 2207/10024; G06T 2207/20221; G06T 2207/30101; G06T 2207/20072; G06T 2207/20076; G06T 7/73; G06T 7/12; A61B 5/7267; A61B 5/7275; A61B 3/12; G16H 50/30; G16H 30/40; G16H 40/67; G16H 50/20
See application file for complete search history.

(56) References Cited

U.S. PATENT DOCUMENTS 8,879,813 B1 * 11/2014 Solanki ................ G06V 40/193
382/128
2015/0265144 A1 * 9/2015 Burlina ................ A61B 3/0025
351/246
(Continued)

OTHER PUBLICATIONS

Burlina et al. "Detection of Age-Related Macular Degeneration via Deep Learning." 13th International Symposium on Biomedical Imaging (ISBI), Apr. 13, 2016, pp. 184-188 (Year: 2016).*

(Continued)

*Primary Examiner* — Jon Chang
(74) *Attorney, Agent, or Firm* — Stephen J. Kenny; Sameer K. Pai; Foley Hoag LLP

(57) ABSTRACT

An automated screening system using retinal imaging to identify individuals with early-stage Age-related Macular Degeneration (AMD) and identify individuals at risk for developing late AMD.

17 Claims, 20 Drawing Sheets

(51) Int. Cl.
*G06T 7/11* (2017.01)
*A61B 5/00* (2006.01)
*G16H 50/20* (2018.01)
*G16H 50/30* (2018.01)
*A61B 3/12* (2006.01)
*G06T 7/12* (2017.01)
*G16H 40/67* (2018.01)

(56) References Cited

U.S. PATENT DOCUMENTS

2016/0174830 A1* 6/2016 Rubin ............... A61B 3/102
   351/206
2021/0279874 A1* 9/2021 Boyd ............... A61B 5/398

OTHER PUBLICATIONS

Defauw et al., "Automated Analysis of Retinal Imaging Using Machine Learning Techniques for Computer Vision," F1000 Research, 5(1573):1-8 (2017).
Hussain, "Automatic Optical Coherence Tomography Imaging Analysis fr Retinal Disease Screening," School of Computing and Information Systems, The University of Melbourne (2017).
International Search Report and Written Opinion for International Application No. PCT/US18/32697 dated Aug. 9, 2018.
Kanagasingam et al., "Progress on Retinal Image Analysis for Age Related Macular Degeneration," Progress in Retinal and Eye Research 23:1-23 (2013).
Rossi et al., "Imaging Individual Neurons in the Retinal Ganglion Cell Layer of the Living Eye," PNAS, 114(3):586-591 (2017).

* cited by examiner

470

```
Patient Name: ...                                              Date .......
ID: ...
Age: ...Gender...History.....

┌─────────────┐                        ┌─────────────┐
    │ CF          │                        │ CF          │
    │ Image       │                        │ Image       │
    │ Left Eye    │                        │ Right Eye   │
    └─────────────┘                        └─────────────┘

┌─────────────┐                        ┌─────────────┐
    │ RF/AF/IR/   │                        │ RF/AF/IR/   │
    │    Enface   │                        │ Enface      │
    │ Image       │                        │ Image       │
    │ LEFT eye    │                        │ Right Eye   │
    └─────────────┘                        └─────────────┘

Summary: Pathology in the left eye; risk score........................
Recommendation/treatment: ....................
```

FIG. 21

IMAGE BASED SCREENING SYSTEM FOR PREDICTION OF INDIVIDUAL AT RISK OF LATE AGE-RELATED MACULAR DEGENERATION (AMD)

CROSS-REFERENCE TO RELATED APPLICATIONS

This application is a continuation of International Application No. PCT/US2018/032697 filed May 15, 2018, which claims priority to U.S. Provisional Application 62/572,292, filed Oct. 13, 2017, entitled "Image Based Screening System For Prediction of Individual At Risk of Late Age-Related Macular Degeneration (AMD)," each of which is incorporated by reference in its entirety herein.

STATEMENT OF GOVERNMENT SUPPORT

This invention was made with government support under SBIR Phase I Grant REY026841A awarded by the National Institutes of Health National Eye Institute.

TECHNICAL FIELD

The present disclosure relates to an automated screening system using retinal imaging to identify individuals with early- and intermediate-stage Age-related Macular Degeneration (AMD), and to predict and identify individuals at risk for progressing to late AMD.

BACKGROUND

Age-related macular degeneration (AMD) is the leading cause of vision loss in those over the age of 50 years in the developed world. (See FIGS. 1(a)-1(d).) The number of people with AMD is expected to increase~1.5 fold over the next ten years due to an aging population, hypertension, and other causes. By the time a person visits an ophthalmologist, it is typically too late. While treatment with anti-Vascular Endothelial Growth Factor (anti-VEGF) is effective in maintaining or improving vision in the neovascular form of advanced AMD (e.g., wet AMD), it does not provide a cure. In addition, such treatments are costly and may be associated with significant cardiovascular risks, or even development of GA. The Age-Related Eye Disease Study (AREDS) showed that specific antioxidant vitamin supplementation (the AREDS formulation) reduces the risk of progression from intermediate-stage AMD (defined as the presence of either many medium-sized drusen or one or more large drusen) to late AMD that can allow for preventative strategies.

Current commercial and noncommercial AMD screening systems have limitations. For example, color fundus (CF) imaging cannot sufficiently detect reticular pseudo-drusen (RPD), a very significant risk factor for wet AMD. (See FIGS. 2(a)-2(b).) In addition, people in remote and underserved areas rarely have access to an ophthalmologist for AMD screening.

Accordingly, there is a need to develop a screening system using retinal imaging to identify individuals with early-stage AMD and at the risk of late AMD.

SUMMARY

A method for identifying individuals at risk of progression from intermediate stage AMD to late stage AMD is provided herein, including receiving retinal image data and socio-demographic parameters; and performing AMD suspect screening which includes performing image data segmentation to prepare a segmented image having prominent regions; performing elastic registration to the segmented image to prepare a registered image comprising the locations of the AMD pathology; generating a matrix from the registered image; training a deep convolution neural network with the matrix data and socio-demographic parameters; and generating a fuzzy weighted score regarding risk of developing late AMD using the deep convolution neural network.

In some embodiments, receiving retinal image data includes receiving color fundus (CF) and red free (RF) image data. In some embodiments, receiving retinal image data includes receiving color fundus (CF) image data. In some embodiments, receiving retinal image data includes receiving red free (RF) image data.

In some embodiments, performing elastic registration to the segmented image to prepare a registered image comprising the locations of the AMD pathology comprises macular area mapping.

In some embodiments, macular area mapping includes identification of the optic disc; identification of major vessel-segments about the optic disc boundary; and identification of the retinal raphe. In some embodiments, macular area mapping further includes detection of the macular center. In some embodiments, macular area mapping further includes selection of a 6000 micron diameter region about the macular center.

In some embodiments, generating the fuzzy weighted score includes use of one or more of random forest, decision stump, support vector machine, or artificial neural network classifiers to predict the risk of progression from intermediate stage AMD to late stage AMD.

In some embodiments, the method includes, prior to generating a matrix from the registered image, generating a normalized image including the prominent features comprising one or more of median filtering, image normalization and Gabor filtering.

In some embodiments, training the deep convolution neural network with the matrix data and socio-demographic parameters includes training the neural network to classify a pixel as RPD/bright lesion or background; mapping each RPD/pathology region; and analyzing the shape and size to determine if the region is soft or hard drusen.

In some embodiments, if the AMD suspect screening provides a score indicative of progression from intermediate stage AMD to late stage AMD, performing an AMD incidence prediction, which includes performing machine-learning on retinal image data comprising analyzing the shape of the region and analyzing the size of the region to distinguish drusen from background image data; performing a graph-based method on retinal image data for drusen quantification comprising normalizing the image data, detecting seed points based on local peak intensity, and detecting an edge around each seed point corresponding to the edge of the drusen; merging the information from the machine-learning and graph-based methods to determine the drusen regions; providing a prediction score;

In some embodiments, if the prediction score indicates late stage AMD providing a treatment regimen; and if the AMD suspect screening provides a score not indicative of progression from intermediate stage AMD to late stage AMD, recommending a repetition of the AMD suspect screening at a future time.

In some embodiments, detecting an edge around each seed point includes applying Dijkstra's shortest path algorithm and analyzing one or more of color, intensity, and texture analysis with Gabor filter bank response.

A system for identifying individuals at risk of progression from intermediate stage AMD to late stage AMD is provided herein, the system including a computer system having one or more processors including a server and a remote device configured by machine-readable instructions to: receive at a server de-identified encrypted retinal image data from the remote device, e.g., color fundus (CF) and/or red free (RF) image data and socio-demographic parameters; and perform AMD suspect screening; and transmit a report from the server to the remote device information regarding AMD stage, risk, and further recommendation to visit an ophthalmologist immediately or at a certain time-frame, In some embodiments, the system includes a re-identification and decryption module at the remote device configured by machine-readable instructions to produce a report of individual's AMD stage with the image, individual's personal and pathological information.

In some embodiments, the AMD suspect screening includes performing CF and RF image data segmentation to prepare a segmented image having prominent regions; performing elastic registration to the segmented image to prepare a registered CF and RF image comprising the locations of the AMD pathology; generating a matrix from the registered CF and RF image; training a deep convolution neural network with the matrix data and socio-demographic parameters; and generating a fuzzy weighted score regarding risk of developing late AMD using the deep convolution neural network In some embodiments, the information transmitted from the server to the remote device includes image data, wherein the images is cropped in the center area for the region of interest based on image center, wherein the image is split into a plurality of parts and merged in the server for faster communication.

In some embodiments, a screening system is provided for identification of an individual who is a suspect, e.g., having early or intermediate stage of AMD. In some embodiments, the system relies on color fundus (CF) retinal image data, red-free (RF) image data, or fusion of color fundus (CF) and red-free (RF) image data. In some embodiments, the system includes a deep learning technique and/or a telemedicine platform. CF and RF images can be segmented for prominent region selection; then elastic registration is applied on the segmented image to find the corresponding positions, e.g., to map the same location. Following this, a 3D cube/matrix can be generated to map the positional information for both imaging modalities. A preprocessing step can be involved to generate the normalized image and prominent features. For this, the median filtering, image normalization and/or Gabor filtering can be utilized. A deep convolution neural network can be applied to identify the normal subjects and AMD suspect or risk subjects.

A prediction model for identifying individuals at risk of developing late AMD with a certain timeline is provided. Once a subject has been identified as AMD suspect, e.g., early or intermediate stage of AMD, a prediction score can be computed for the individual at risk of developing late AMD. For this, pathology quantification can be performed, utilizing image segmentation, AMD pathology identification, categorization and quantification. (Retinal image segmentation can include CF data, FR data and/or a fusion of CF and RF image data.) These parameters can be used along with sociodemographic parameters and 3D matrix generated from a registered image to train a deep convolution neural network. The dense layer of the deep convolution network accepted the optimized features after principal component analysis. A Support Vector Machine based on the non-linear regression model is also utilized to fuse the features. The machine learning classifier can be used to predict the individual at risk of developing late AMD by utilizing cross-sectional data. If the individual's longitudinal images and data are available (e.g., available through multiple visits), additional parameters are applied. For this, corresponding changes for each of the pathology areas, in addition to the parameters discussed herein, are taken into account to predict that the individual is at risk of developing late AMD. The deep convolution neural network can also be trained differently for cross-sectional and longitudinal data analysis. The retinal mages (e.g., the CF, the RF, or fused CF/RF data) are registered and a 3D matrix is constructed. Then deep learning can be applied to this new data format, e.g., if there is only one patient visit. If data from multiple visits is available, image difference is applied in each corresponding layer, utilizing elastic registration, and these matrices are used to train the deep convolution neural network.

A telemedicine platform is provided for integrating the AMD screening and prediction engines, along with, e.g., remote computer, mobile or handheld device applications, to interact with patient, doctor and healthcare providers. on the client side, the actual data is deidentified and encrypted. The telemedicine platform integrates the server (e.g., where the image analysis, machine learning and deep learning modules for AMD severity screening are stored) and local remote computer, tablet or mobile devices (for patient data and images taken by retinal portable camera). To make this image-based AMD screening system widely available in both urban and rural/remote underserved areas, a telemedicine platform can be utilized to exchange the data securely. The remote devices upload the de-identified encrypted images and data to the server to analyze the images and screen AMD automatically. The automatic analysis is performed and a report is sent to the patient/remote devices with AMD stage, risk, and further recommendation and to visit an ophthalmologist immediately or at a certain time frame. The images can be cropped in the center area for region of interest that is based on image center. Also, image can be split into four parts and merged in the server for faster communication. A re-identification and decryption module produces a report of individual's AMD stage with the image and the individual's personal and pathological information.

A technique for macular area mapping of the color fundus (CF) image and finding the macular area in red free (RF) image by registering the CF and RF image is provided. The technique includes, e.g., combining the left-eye and right-eye information, image region selection, optic disc identification, center computation, major vessel-segment identification above and below the optic disc boundary, retinal raphe identification and macular center detection and 6000 microns diameter region selection.

A technique for quantifying drusen in color fundus (CF) image is provided. The technique includes the fusion of output features obtained from the edge and Dijkstra's shortest path algorithm based drusen quantification along with one or more of color, intensity, and texture analysis with Gabor filter bank response and machine learning algorithm.

A technique for quantifying reticular pseudo drusen (RPD) in red free (RF) image is provided. The segmentation model is substantially identical to that used in CF for drusen is used to quantify RPD for RF imaging. In one embodiment for RF image data, only the normalized intensity information is used along with texture. Using the feature vectors, the neural network is trained, and pixels are classified as RPD/ bright lesion and background. Following this, each RPD/ pathology region is mapped, shape and size are analyzed, and a determination is made whether it is a soft or hard drusen.

In some embodiments, the focus is in the 3000 and 6000 μm radii of the macular area, where RPD usually occur. The characteristic RPD clustering in a single, well-defined region is used to differentiate them from drusen, which are usually randomly distributed in several small regions.

The RPD can be quantified by using other image modalities such as Fundus autofluorescence (AF), Infrared (IR), and Grayscale image (e.g., enface image) instead of red free (RF) imaging. The method RPD quantification can be applied in AF or IR or enface image for the reticular pseudodrusen quantification and add this information in the AMD severity level computation.

In some embodiments, a report is provided in which the quantified pathologies along with the risk score for an incident of late AMD are supplied.

BRIEF DESCRIPTION OF THE DRAWINGS

The foregoing and other objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein

FIG. 21 illustrates a final report in accordance with exemplary embodiments of the disclosed subject matter.

DETAILED DESCRIPTION

The embodiments will now be described more fully hereinafter with reference to the accompanying figures, in which exemplary embodiments are shown. The foregoing may, however, be embodied in many different forms and should not be construed as limited to the illustrated embodiments set forth herein.

Figure 3:
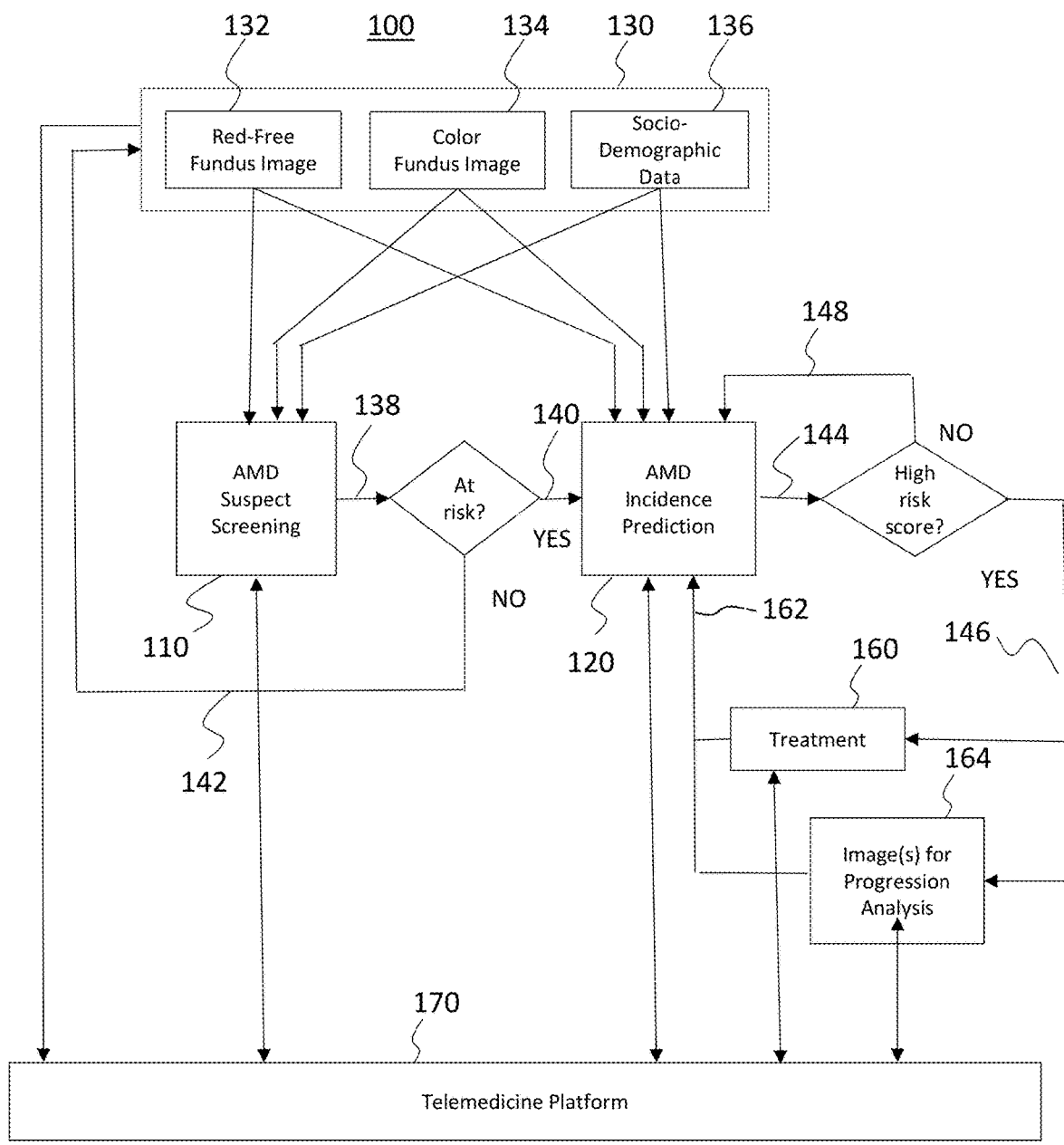
FIG. 3 is a schematic diagram of a system for AMD suspect screening and prediction of Late AMD in accordance with exemplary embodiments of the disclosed subject matter.

A multimodal color Fundus (CF) and red-free (RF) image analysis platform for AMD screening and prediction system is illustrated in FIG. 3. The system includes two modules. First, a module for automated screening of individuals for early-stage AMD 110 is provided (see also, FIG. 4). Second, a module for prediction of individuals at risk of developing late AMD in the near future 120 is provided (e.g., six months to two years) (See also, FIG. 5).

The AMD screening and prediction technique includes two steps. (Not all individuals being screened will be subject to both levels of screening, as will be discussed herein.) First, data from an individual is screened to determine whether they are suspected of having AMD, e.g., being "at risk" for AMD. Second, once a suspect is found, a prediction score of the risk of progression to late AMD in the near future is calculated for that individual. The ophthalmologist can use this risk score to make a decision of start AMD treatment and prevent the development of AMD. In some embodiments, both steps, the executables programs, and data are deployed on the server, and a secured telemedicine platform is used to exchange the patient information from client devices and the server with maintaining high security and privacy.

An exemplary embodiment of the system is illustrated in FIG. 3. The system includes an AMD suspect screening module 110 and the AMD incidence prediction module 120. The screening module 110 receives patient data 130. Patient data 130 includes, e.g., red-free (RF) fundus data 132, color fundus (CF) data 134, and socio-demographic data 136. The output 138 of screening module 110 is a determination of whether the individual is suspected to be "at risk" of AMD. If the determination is that the individual is at risk ("YES") at 140, the individual is referred for execution of the AMD incidence prediction module 120, e.g., with an ophthalmologist. If the individual is determined to be not "at risk" of AMD ("NO") at 142, the individual is referred to return to the ophthalmologist for screening later, e.g., in a year.

The output of the AMD incidence prediction module 120 is a prediction score 144 regarding the risk of development of late AMD in the near future, e.g., 6 months or 2 years. If the prediction score is "high," at 146 (as described in greater detail below), the individual is determined to be at high risk. Treatment 160 is started for high risk patients, and follow up 162 with analysis by the AMD incidence prediction module 120 is recommended every four months. The systems and methods described herein provide the individual with the opportunity for treatment far earlier than would be provided under conventional techniques. Early detection under the techniques described herein focuses on the early stage and intermediate stage of AMD. Early detection will enable the patient to benefits from treatment, for example, vitamin and mineral supplements, exercise, cessation of smoking and other preventative measures by AREDS protocol. By taking such measure earlier, the patient can prevent the incident of late AMD. If the score is determined to be "not high" 148, then the patient will be advised to revisit after 6 months or one year depending on the eye condition.

Figures 1A, 1B:
FIG. 1(a) is a photographic representation of an image seen by a person with normal vision.
FIG. 1(b) is a photographic representation of an image seen by a person with late AMD.
Figures 1C, 1D:
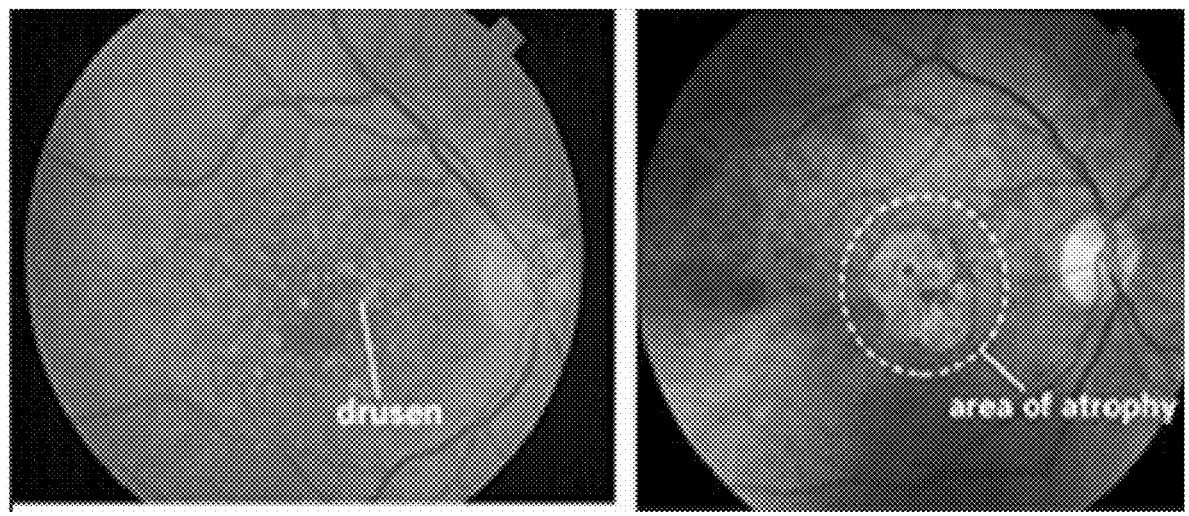
FIG. 1(c) is a black and white representation of a retinal color fundus (CF) image illustrating AMD pathology.
FIG. 1(d) is a black and white representation of a retinal color fundus (CF) image illustrating geographic atrophy.
Figure 2A:
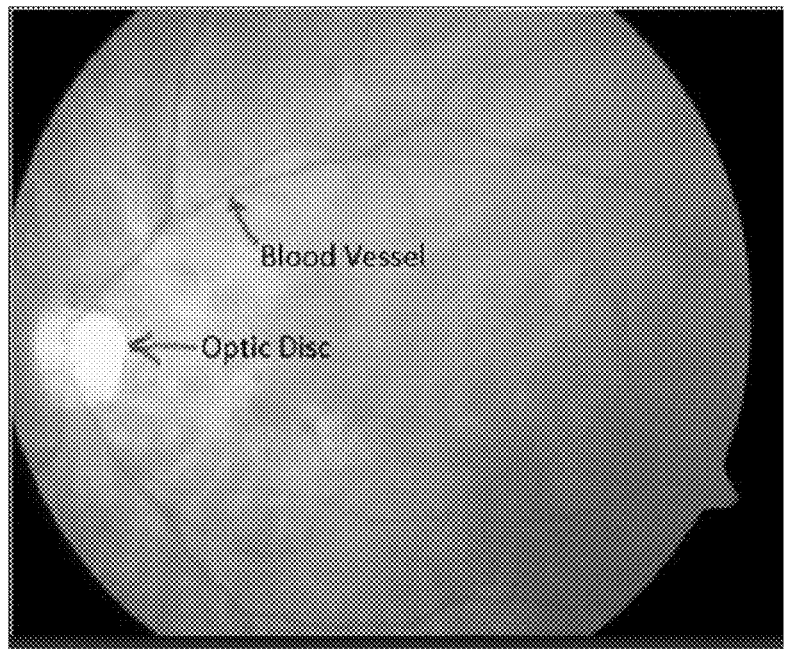
FIG. 2(a) is a black and white representation of a color fundus (CF) image that does not show RPD in the eye.
Figure 2B:
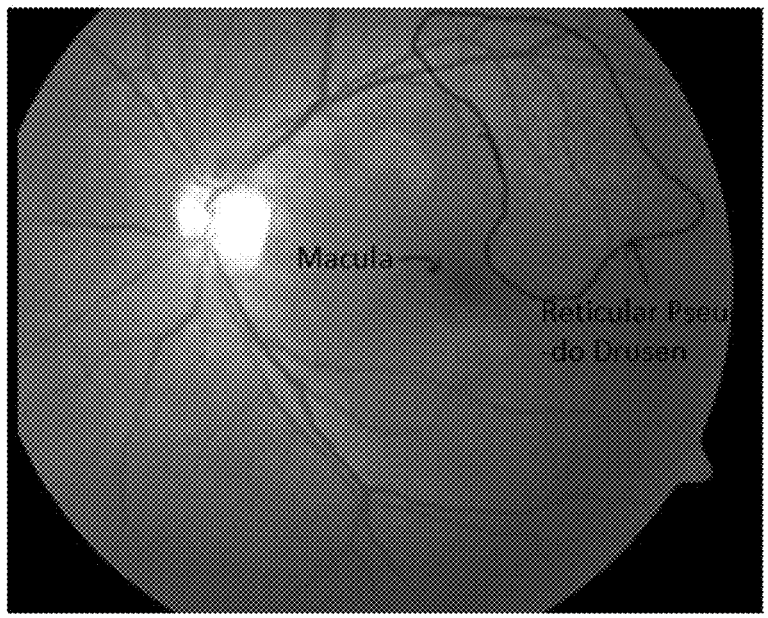
FIG. 2(b) is a Red-Free image showing RPD in the same eye as FIG. 2(a).

The AMD screening system 100 utilizes machine-learning-based algorithms for extraction of features (e.g., AMD pathologies) and fusion from multimodal imaging and deep convolution neural network. In some embodiments, the system uses CF image based features only. In some embodiments, the system uses RF image based features only. In some embodiments, the system fuses CF image-based features (see FIGS. 1(c), 1(d) and 2(a) and RF image-based features (see FIG. 2(b)), which are used complementarily to extract AMD pathologies (e.g., drusen and RPD) and identify individuals at risk of developing late AMD.

Figure 4:
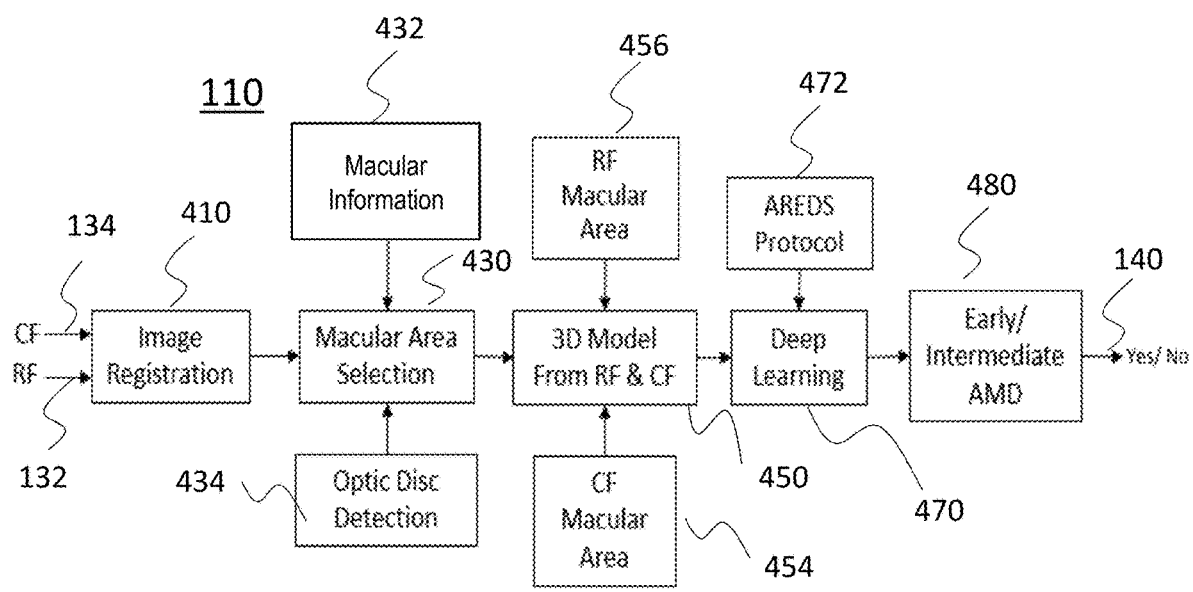
FIG. 4 is a schematic diagram of a system for AMD suspect screening in accordance with exemplary embodiments of the disclosed subject matter.

FIG. 4 illustrates the components of the AMD suspect screening module 110 described above. At Step 410, CF images (or RF or fused CF and RF images) are segmented for prominent region selection; then elastic registration is applied on the segmented CF images (or RF or fused CF and RF images) to find the corresponding positions of the potential AMD pathology, e.g., to map the same location (Step 430).

Following this, generation of a 3D cube/matrix to map the positional information is performed (Step 450). After the CF images (or RF, or fused CF and RF images) are registered, a matrix is constructed from these two imaging modalities, e.g., the RF macular area 456 and the CF macular area 454. In some embodiments, the color image has three layers and RF image has one layer. Accordingly, the matrix has four layers in the depth dimension that are aligned with the registration coefficients for the pixel positions. That is, superimposing the imaging modalities based on correct positional alignment and increase the number of layers in the depth. It is referred to herein as a 3D matrix, as it converts the 2D imaging into a 3D non-imaging format.

A preprocessing step (not shown) can be used to generate the normalized image and prominent features. In come embodiments, median filtering, image normalization, and Gabor filtering are utilized.

Deep learning and image analysis are applied (step 470) to identify the normal/healthy individuals, and AMD suspect individuals. As the output of the analysis (480), an individual is determined to be either "at risk" or not "at risk."

If an individual determined to be not "at risk" for AMD, the individual is advised to return in one year, as shown in FIG. 3 (Step 142). If an individual is determined to be "at risk" for AMD 140, the individual's data is then processed by the AMD incidence prediction module 120, which includes feature and/or longitudinal image analysis, e.g., to be provided to an ophthalmologist for a high confidence diagnosis. Following the analysis, treatment 160 and/or follow up 162 are prescribed. Further, an image is taken for progression analysis 164. Data are shared to the telemedicine platform 170, as will be described in greater detail herein.

Figure 5:
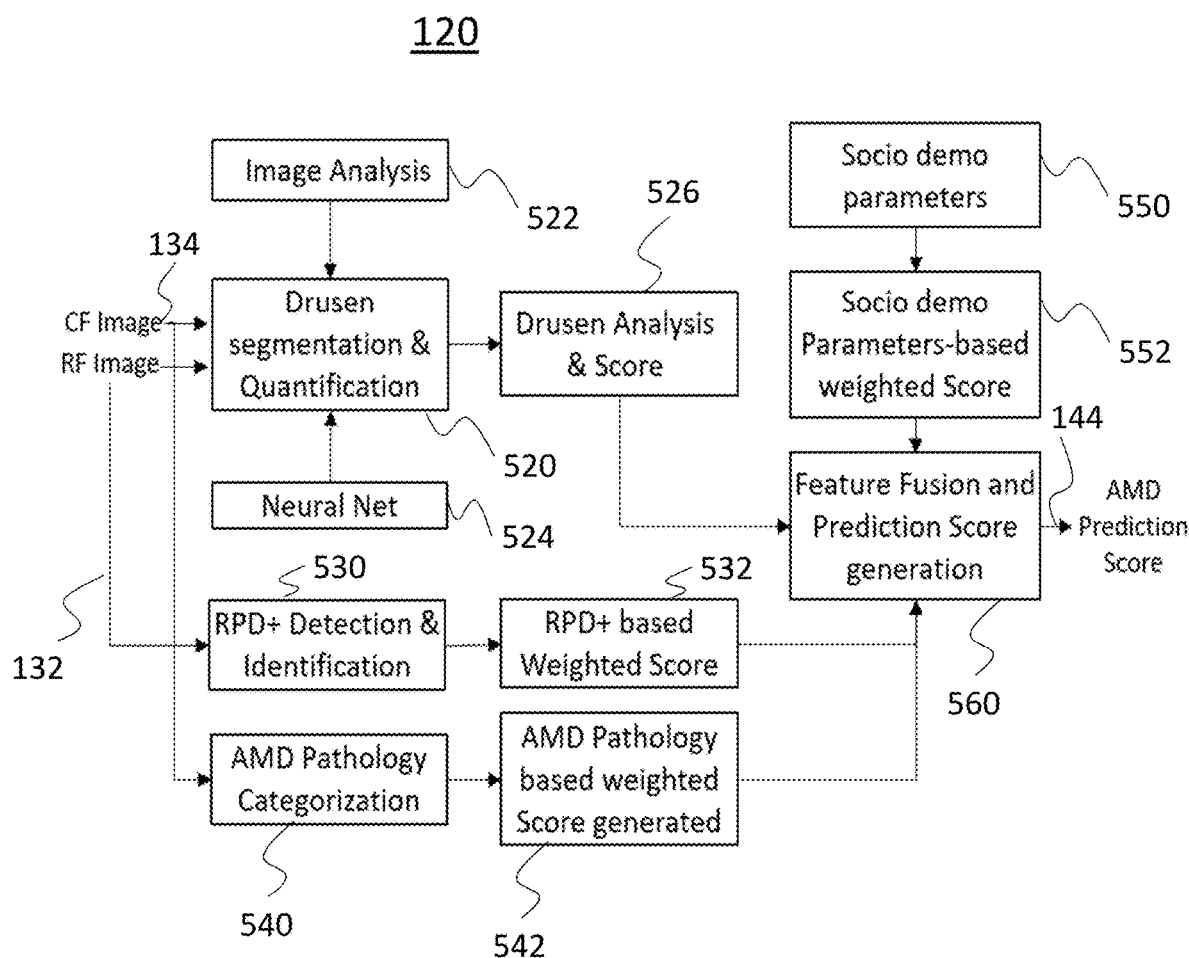
FIG. 5 is a schematic diagram of a system prediction of Late AMD in accordance with exemplary embodiments of the disclosed subject matter.

A prediction module 120 for predicting individuals at risk of late AMD is illustrated in FIG. 5. Once an individual is identified as "at risk" by the AMD Suspect screening module 110, a prediction score 144 for the individual for developing late AMD in near future is computed by the AMD incidence prediction module 120. The pathology quantification is performed utilizing the CF images 134 and RF images 132 to find the prediction score of that individual for developing late AMD. The CF and RF images are registered with finding the best transformation parameters (rotation, scale, and translation) for registration of two images based on the segments of the retinal vessels. These parameters, along with socio-demographic parameters for a training machine learning classifier, are used to predict the individual at risk of developing late AMD by utilizing cross-sectional data.

If the individual's longitudinal images and data are available (e.g., through multiple visits), corresponding changes over time to the pathology areas, in addition to the mentioned parameters, are used to predict the individual at risk of developing late AMD. The corresponding pathological changes are computed through the elastic registration of the color images taken on different visits. The same procedure is applied for red-free (RF) images. A deep learning model is used to predict the individual at risk of AMD. The RF and CF images are registered, and a 3D matrix is constructed from these two imaging modalities. Deep learning is applied to this new data format if there is only data from one patient visit. If there is data for a patient's multiple visits, the difference in the 3D matrix is applied to each corresponding layer utilizing the elastic registration and using these matrices to train the deep convolution neural network.

Figure 6:
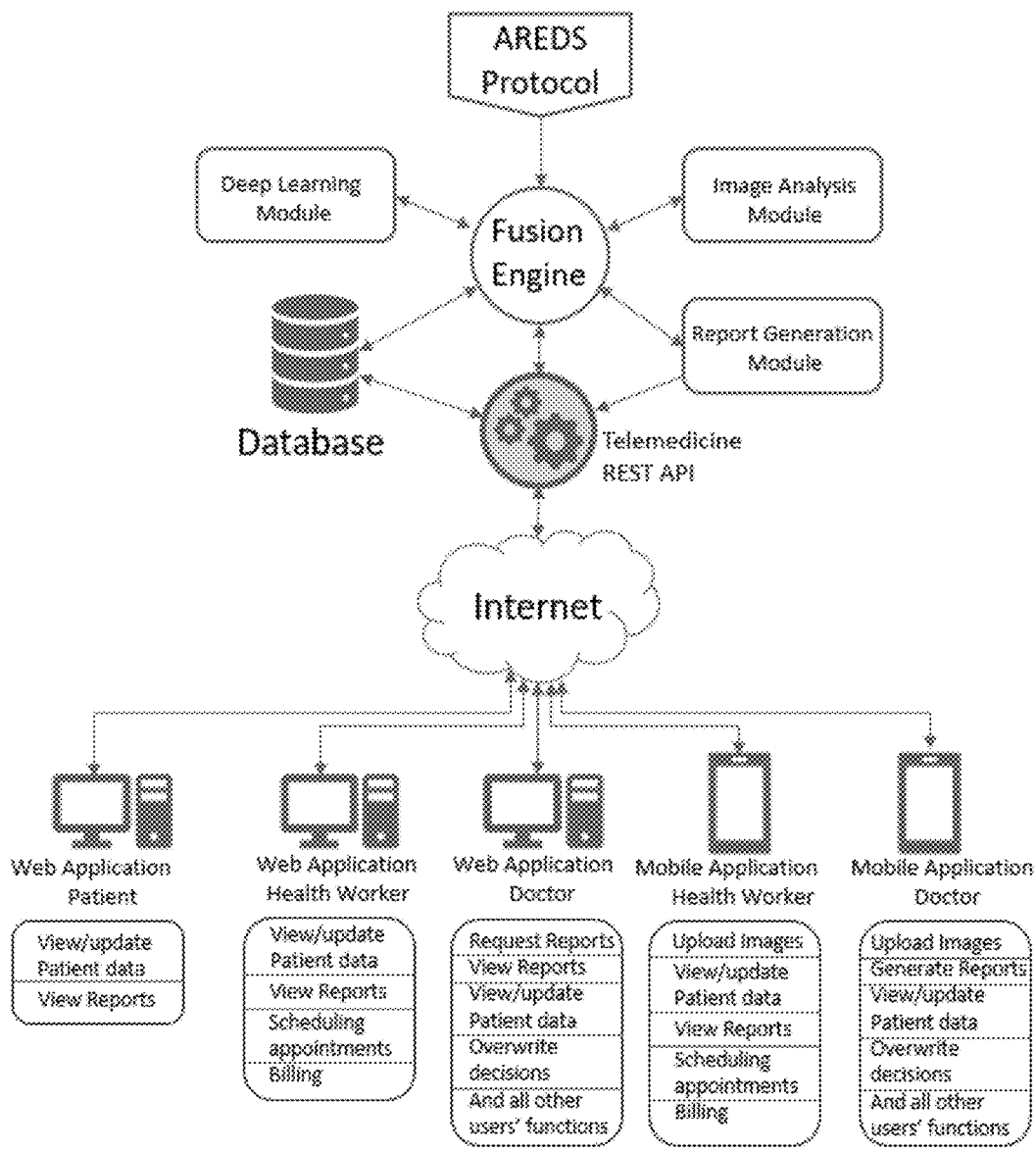
FIG. 6 is a schematic diagram of an overall platform for telemedicine in accordance with exemplary embodiments of the disclosed subject matter.

To make this image-based AMD screening system widely available in both urban and rural/remote underserved areas, a telemedicine platform (FIG. 6) is utilized to exchange the data securely. In some embodiments, the telemedicine platform integrates the server (where the novel image analysis, machine learning and deep learning modules for AMD severity screening can be stored) and local remote computer, tablet or mobile devices (for patient data and images taken by the retinal portable camera). The remote devices upload the de-identified encrypted images and data to the server to analyze the images and screen AMD automatically. The automatic analysis is performed, and a report is sent to the patient/remote devices with AMD stage, risk, and further recommendation and to visit an ophthalmologist immediately or within a certain time frame. The re-identification and decryption module produce the report of individual's AMD stage with the image, individual's personal and pathological information.

Figure 7:
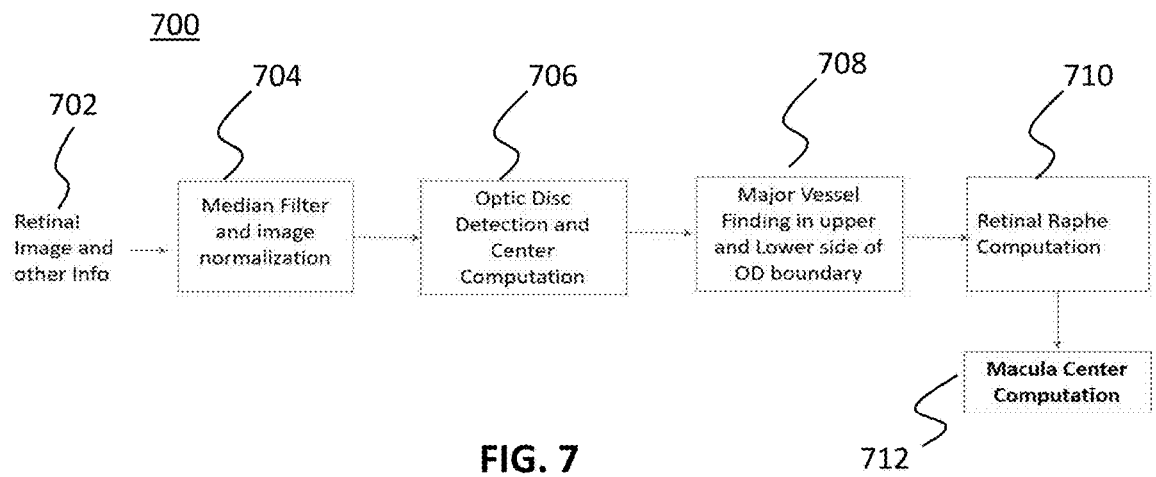
FIG. 7 is a flow chart for macular center detection techniques in accordance with exemplary embodiments of the disclosed subject matter.

As illustrated in FIG. 7, a method for macular area mapping from CF imaging is described. The macular center detection method obtains the pathologies from the macular area to follow the international AMD grading protocol, for example, 6000 microns diameter about the macular center. In this method, the left eye and right eye information are utilized among other information as described herein. The following exemplary steps are provided in the following exemplary order: Median filter and image normalization are performed (Step 704). The optic disc (OD) is detected, and the OD center is calculated (Step 706). Next, major vessel finding in upper and lower side of the OD boundary is performed (Step 708). Vessel width information and vessel segment information originating from the optic disc are computed. Vessel segments are selected which extend into the upper or lower part of the image originating in the OD center. For example, major vessels are selected by computing the width. Using these determinations, the retinal raphe computation is performed (Step 710). An average angle is computed for the upward vessels (towards upper orchid) with respect to the image horizontal line. Similarly, an average angle is computed for downward vessels (towards lower orchid). Following this, the angle is computed from the average upward and downward vessel angles in the OD center. The line (e.g., retinal raphe) is computed which is passing through the middle of this angle. Next, macula center computation is performed (Step 712). The macular center is determined as point in this line which is at a distance of 2.5 times the OD diameter away from the optic disc center. A circular region around 6000 microns (radius) of the macula center is then mapped.

Figure 8:
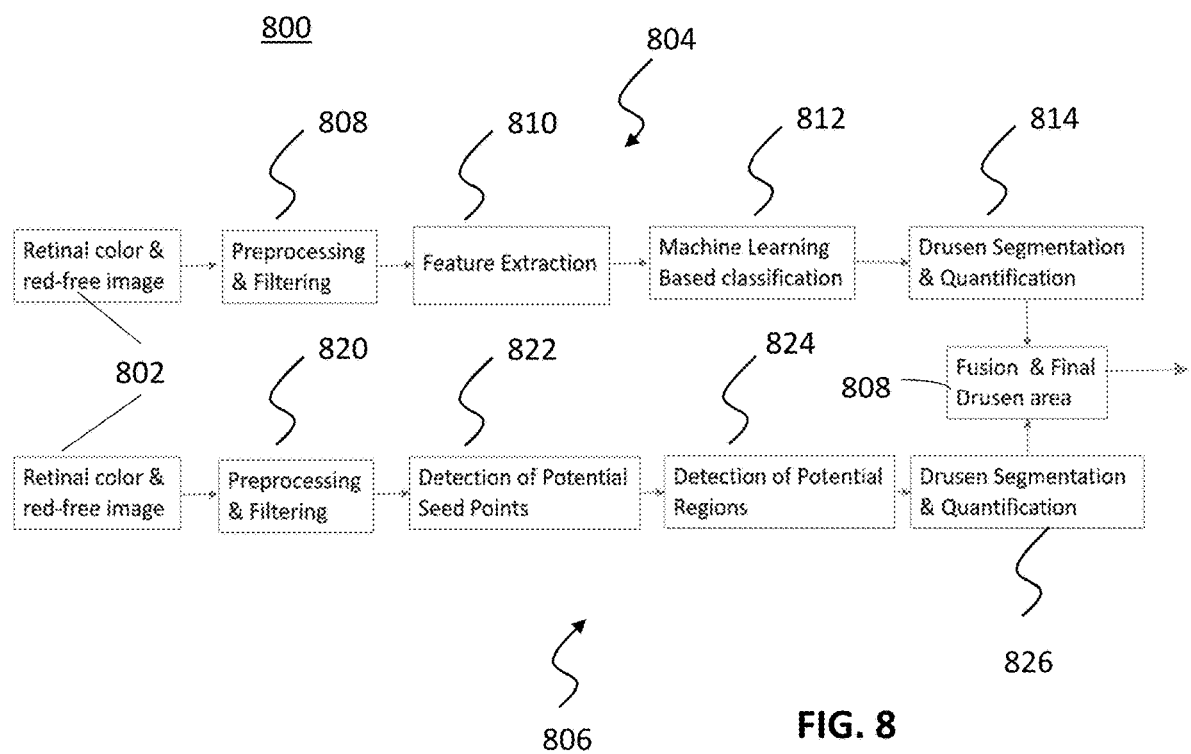
FIG. 8 is a flow chart for Drusen segmentation and quantification in accordance with exemplary embodiments of the disclosed subject matter.

A method for drusen quantification during AMD incidence prediction 120 is illustrated in FIG. 8. The quantification provides "early," "intermediate," or "late" AMD stage classification along with categories 1-9 discussed herein. A machine-learning method 804 and a graph-based method 806 for drusen quantification are applied to the retinal color and red-free image data 802, which are then merged to determine the drusen regions (Step 808):

In the machine-learning method 804, the drusen are detected and quantified using CF imaging and RPD imaging, and RPD from RF imaging. For red-free and color image analysis for hard and soft drusen quantification, the normalized intensity, edge, and shape information are utilized. For soft drusen and RPD quantification in CF and RF image—color, texture and normalized intensity information are used for each pixel to construct the feature vector (808, 810). At step 812, the Backpropagation artificial neural network (ANN) (524) is used to train the AMD prediction incidence module 120 using ground truth images marked as "drusen/pathology" and "normal" pixels that have been segmented by an expert grader for drusen areas. This is supervised technique for drusen and bright lesion segmentation to provide drusen segmentation and quantification (Step 814).

In the graph-based method 806, a normalization technique is applied that solves that uneven intensity distribution. Following preprocessing and filtering (Step 820), the seed points of drusen are detected with the robust technique (Step 822), from which potential drusen regions are detected using border pixels of the drusen and graph-based methods (Step 824). Finally, the intensity ratio between potential regions and background are used to finalize the actual drusen. In the segmented image, the regions are tracked, and shapes and sizes are analyzed to define hard drusen, soft drusen or other pathology.

Figure 9:
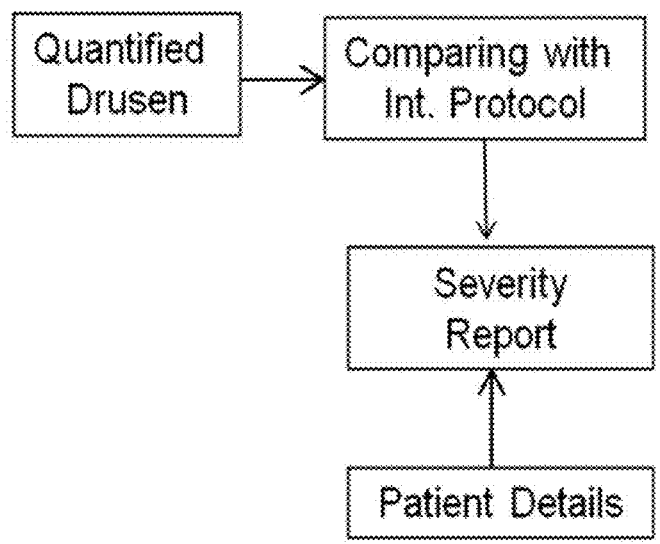
FIG. 9 is a flow chart for report generation in accordance with exemplary embodiments of the disclosed subject matter.

A technique for report generation on AMD status and pathology information is illustrated in FIG. 9. The left eye and right eye macula center images are included with marked pathologies and focus macula area (6000-micron diameter). The report provides the AMD risk status and the risk score of future incidence of late AMD along with the necessary advice for ophthalmologist visit within a certain time frame (e.g., immediate or in a month).

Figure 10:
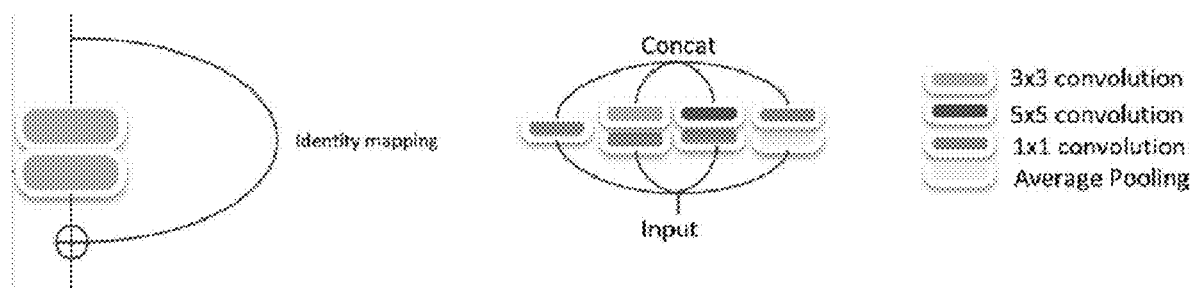
FIG. 10 is a representation of residual mapping (left) and a typical Inception module (right) frameworks in accordance with exemplary embodiments of the disclosed subject matter.

AMD Suspect Screening with Image Analysis and Deep Convolutional Neural Network 470 (ConvNet). The AMD suspect screening system 110 (FIG. 4) is based on the macula area mapping in CF image, registering CF and RF images to map the macula area in RF image, drusen segmentation and quantification in CF image and RF image, RPD segmentation and quantification in RF image, and the quantified features for early and intermediate AMD severity measurement, individual's socio-demographic parameters and deep convolution neural network 570 (FIG. 10). The macula area is selected based on the International Classification and Grading System for AMD. The protocol considers three circles with diameters of 1,000, 3,000, and 6,000 μm centered on the macula. The image registration confirms the alignment of CF and RF images centered in the macula. Registration also maps the same location and identifies the drusen area changes which will be used in the prediction module.

Macula area mapping in CF image. Macula area mapping module maps the macula area within 6000 microns radius around the macula center. This is to follow the AREDS AMD grading protocol for extracting the drusen and other AMD pathological information around the macula area. Macula area mapping works in two steps—(1) optic disc center detection 534 and (2) macula center detection 532. For macular area detection the following information is used: 1) identification of Left eye or right eye, 2) optic disc information 3) major blood vessel information in above or below the boundary of the optic disc and 4) retinal raphe information When the image is captured during a patient visit, identification of which eye is being scanned (left eye or right eye), along with macula center and disc center information, are input. Left eye or right eye information and macula center image information assists in determining the region of interest to find the optic disc area and center. For example, for left eye and macula center, the optic disc is in the right side of the image, and thus the right portion of the image is searched to achieve efficiency.

Figure 11A:
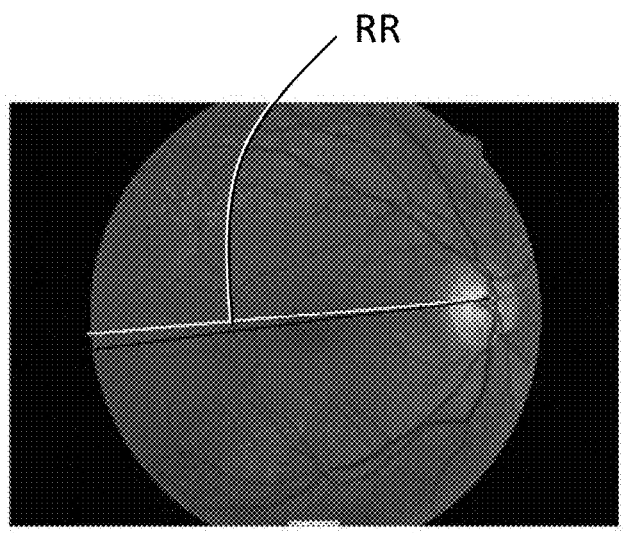
FIG. 11(a) is an image of the retinal raphe.

Macula Area Detection. An early step in the process is to determine the location of the retinal raphe RR, a line that passes through the macula center (FIG. 11(a)) The Macula center is known to lie along the retinal raphe at an approximate distance of 2.5 times the OD diameter away from the optic disc center. The macular detection algorithm uses this spatial relationship between the OD and macula to locate the macula center. The retinal raphe is somewhere within 30 degrees above or below the line connecting the optic disc to the center of the object of interest.

Figure 11B:
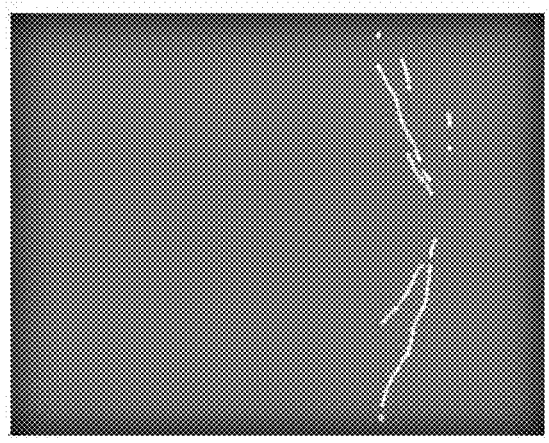
FIG. 11(b) is an image of the centerline of vessel segments.
Figure 11C:
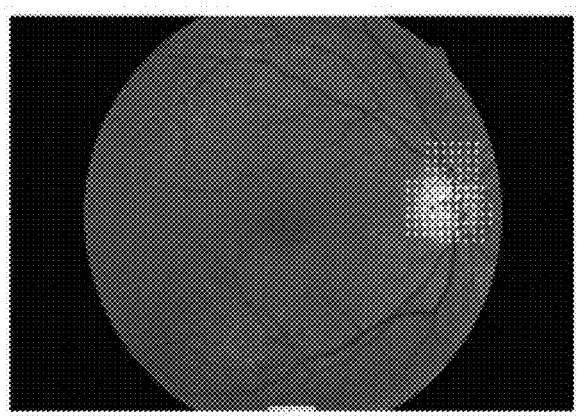
FIG. 11(c) is an image of the density of branch points.
Figure 11D:
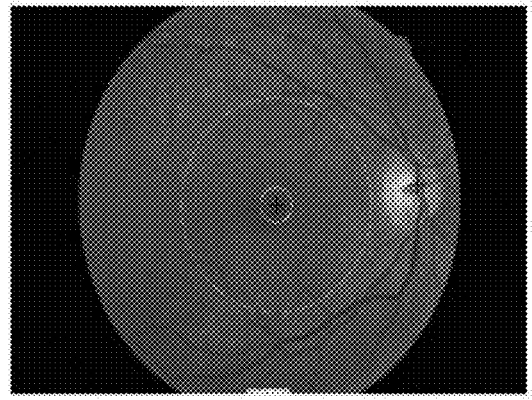
FIG. 11(d) is an image of the OD (optic disc), macula center, and macular area mapping.

Thus, the angle of the retinal raphe is determined by using the angles of the blood vessel centerlines radiating from the OD center (See, FIG. 11(b)) and using this line to locate the macula center. Blood vessel centerline detection is based on the method described in PCT application PCT/US17/41712, which is incorporated by reference in its entirety herein. A Gabor filter bank is applied for texture analysis to cluster the pixels into vessel and non-vessel using Otsu's filter. In an exemplary embodiment, all angle calculations are made in radians with a range 0 to $2\pi$. Angles are automatically converted such that they stay within these limits unless stated otherwise.

For optic disc detection: Once the vessel-segments are determined, their crossing points in the right or left quadrant of the columns are analyzed. The number of vessel crossover points (two vessels cross the point) is usually large in the optic disc center region. Intensity thresholding is applied based on top 10% of the highest intensity pixel values. Then the intensity values are thresholded and Canny edge is applied to determine the circular or oval-shaped edge, e.g., optic disc. The number of crossover points is determined, and the center of the optic disc is found through computing the circular edge centroid value.

A vessel width measurement technique is applied in the regions focusing on above and below the optic disc. The vessel width is based on Canny edge detection and parallel edge tracking. Once the parallel edge is mapped to determine a vessel, the opposite edge pixels are mapped, and the distance from one edge pixels to the other edge pixels within a certain number is found. Then the minimum distance is the measured width for that vessel cross-section, which is the width. The average width of the vessel-segment is measured, and the major vessel segment just above and below the optic disc boundary is determined.

Finally, the slope of the top two major vessel-segments on above and below the optic disc boundary is computed. The average slope of the top two vessel-segments (the first and second widest vessel) is measured. Similarly, the average slope of the bottom-two top vessel-segments is measured. The angle between these two slopes is computed. The line which splits the angle into half is determined as retinal raphe.

Finally, the macula center is located, which is in the retinal raphe and 2.5 times the OD diameter away from the optic disc center. After mapping the macula area, the cropped image is produced for macula in 6000 microns diameter that is centered at macula center.

Machine Learning based Drusen and bright lesion segmentation 804. For drusen and bright lesion segmentation, Gabor feature analysis is applied, and color features are normalized to train the neural network and classify a pixel as drusen/bright lesion and background. The overall method for drusen and bright lesion segmentation is shown in FIG. 8.

Gabor Feature Set Generation.

Gabor filter bank is applied with varying phase (from 5 to 11) and orientation (0 to $2\pi$). The maximum response of the various orientation and wavelength that were used for vessel segmentation are used here. This output is then used with the color features to train the Neural Network.

Color Feature Generation.

Independent color space information along with normalized RGB, and HSV color information is used. Generally, image data is given in RGB space (because of the availability of data produced by the camera apparatus). The definition of the intermediate system also known as the CIE XYZ space (ITU-Rec709).

Finally, the feature vector is constructed with the parameters Gabor filter response, Red, Green, Blue, Hue, Saturation, CIE X, CIE Y, CIE Z, $3^{rd}$-channel-HSV, R-B, 2*G-R-B). Following this, the neural network is trained to classify pixels as normal and drusen.

Drusen and Bright Lesion Pixel Classification.

Backpropagation neural network (524 in FIG. 5/812 in FIG. 8) was used to classify the pixels into drusen and background or normal. The input vector is the length of 12, and output class number is 2 (drusen/bright lesion and background). Hence, 12 Nodes in Neural Network Input Layer, 12 Nodes in Hidden layer and 2 Nodes output layer are used. Adjust settings such a number of iterations as well regularization parameter (MOMENTUM, LEARNING RATE). To avoid over sampling, the training set is randomly arranged. A subsection is used as a test set to test performance. Once the output is produced in the test phase, noise removal and further filtering is used to select actual areas of drusen and background.

Filter Discrete Noise Points.

Discrete noises due to impulse noise and background irregularities are removed by measuring the area or number of pixels. After detecting the regions, individual regions are traced based on the detected regions. Finally, regions having area or number of pixels less than a certain threshold are discarded and otherwise, assigned a unique identification number for each region.

Drusen Detection.

After noise removal, the size and shape of each region are analyzed to detect the region as a druse as follows: The potential regions that are the edges of the objects in the image are detected, and the size and shape of the objects are checked. Individual regions are traced, and a unique identification number is assigned for each of the regions. Following this, in some embodiments, the size and shape for each of the regions is analyzed as follows:

Drusen Shape Analysis.

A druse is a circular or oval-shaped region. These shapes are 2-D and can be represented using a real or complex 1-D function. The approached described herein is to determine the shape of the identified regions, to verify whether it is circular or oval, using the boundary and centroid. In the first variation of the idea, the values of the 1-D function for circular or oval shapes are equal to distances between the centroid and boundary points. Boundary points are selected so that the central angles are equal. In this approach, the distance between subsequent boundary points for the 1-D function values are used, and the ratio of the minimum and maximum radius are computed to determine the shape as circular or oval. Drusen with shapes different from circular or oval are discarded at this stage.

Drusen Size Analysis.

Figure 12A:
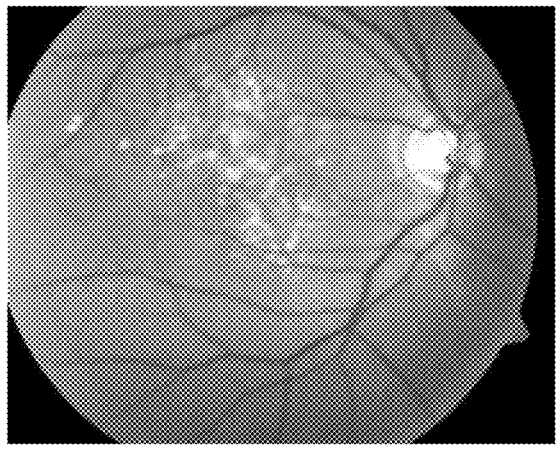
FIG. 12(a) is a retinal gray scale image.
Figure 12B:
FIG. 12(b) is a processed image for drusen detection output in accordance with exemplary embodiments of the disclosed subject matter.

After shape filtering, drusen are filtered based on the size. Since all remaining drusen are now either circular or oval shaped, the diameter of the region provides the size of the region. In this study, the diameter of each shape-filtered drusen is calculated, and then regions with a diameter more than 600 microns (1 pixel=7 microns in the image set; can vary with camera calibration) are discarded. These size-filtered regions are finally detected as the drusen of the retinal image. An image with drusen output shown in FIG. 12(b).

Define and Quantify True Drusen Areas.

Each druse detected in the gradient image is inversely mapped in the druse image using the center of the druse. The true area is calculated based on the druse boundary and region information from the image that includes drusen.

Calculation of individual druse area allow mapping of individual size and the total drusen area in the macula, which allows definition of the severity of early AMD. For each druse, the number of pixels is counted, and the area in microns is computed. The calibration factor between the pixels per distance is utilized for finding the area in microns. Seeded region growing techniques are used to map the pixels belonging to each region that was identified earlier as drusen. Finally, a summary of drusen based on the size in diameter and area is provided.

Graph and edge-based drusen Quantification 806. Drusen are bright in intensity in the color fundus or red-free images. It is very challenging to detect drusen due to the presence of noise in the images that make the uneven distribution of intensity in the homogeneous regions. A technique that can detect drusen while addressing those challenges is described herein. A normalization technique is applied that solves the uneven intensity distribution. The seed points of drusen are detected with the robust technique. Potential drusen are then detected using border pixels of the drusen and graph-based methods. Finally, the intensity ratio between potential regions and background are used to finalize the actual drusen. The flow diagram of the method is shown in FIG. 8. In some embodiments, the method is worked around 6000 μm from the macula where the optic disc is located outside of the search space. Details of the technique are described in the following subsections.

Normalization.

Use the normalized pixel values. Color fundus or red-free images contain noises that create an uneven distribution of intensity even in a homogeneous area of the image. This is a significant challenge for detecting substructures and pathologies such as drusen. A robust intensity normalization technique is applied that solves this challenge robustly using following formula.

$$I'_{x,y} = \frac{I^m_{x,y}}{I^M_{x,y}+1} \quad I''_{x,y} = \frac{I'_{x,y}}{\sqrt{|I'_{x,y}-\overline{I'}|^2}}$$

$$I'''_{x,y} = \frac{0.5 \times I''_{x,y}}{\overline{I''}} \quad I^n_{x,y} = \begin{cases} I'''_{x,y} & \text{if } I'''_{x,y} < th \\ th & \text{otherwise} \end{cases}$$

Figure 13:
FIG. 13 is an original retinal image.
Figure 14:
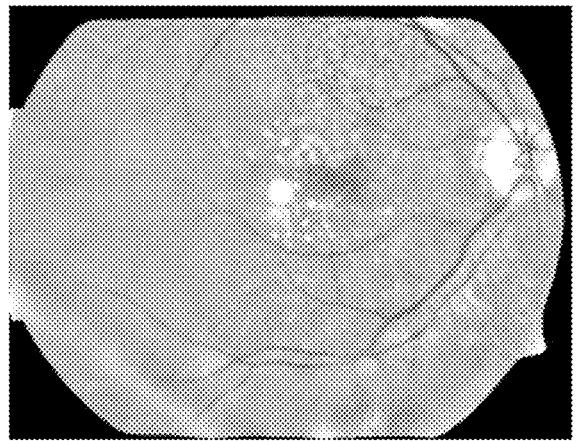
FIG. 14 is a normalized image of FIG. 13 in accordance with exemplary embodiments of the disclosed subject matter.

Where, l''' and l''' are the image after applying median filter with 3×3 and 80×80 window respectively. $\overline{I'}$ and $\overline{I''}$ are the mean value of the image I' and I''. $I_{x,y}^n$ is the normalized intensity at pixel position (x,y). Due to image acquisition environment and pathologies, image could have few pixels with extreme intensities. The assumption is that they are not more than 1%. According to this assumption, a threshold value (th) is defined by the minimum value of top 1% intensities of the image and replace the pixels value which have more than th intensities by th. FIG. 13 is an original image and FIG. 14 illustrates the normalized form.

Detection of the Potential Seed Points.

Figure 15:
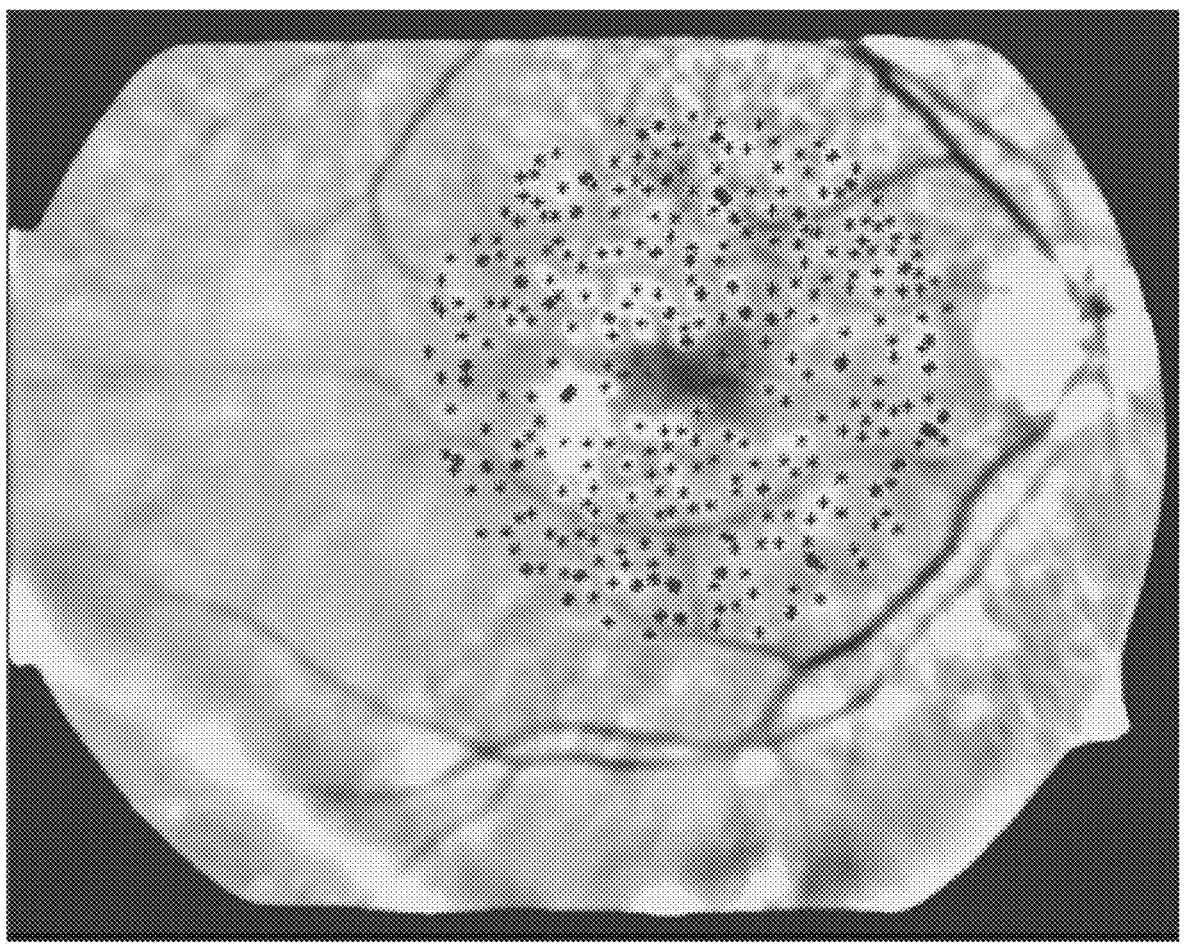
FIG. 15 is a processed image illustrating potential seed points of the drusen image in accordance with exemplary embodiments of the disclosed subject matter.

Drusen have higher intensity values and center of a druse is the top most intensity in its region. Therefore, the center of a druse is a pixel which has local peak intensities in both x and y-axis. The potential centers of drusen are detected as the potential seed points. A Gaussian filter with 5×5 window and two standard deviations is applied three-times for smoothing the image and reducing intensity distortion effect of noise and pathologies which ever left in the normalized image. This smoothing operation blurs the edge of the objects that are not suitable for border detection of an object. Since the aim is finding the centers of drusen, this blurring helps to avoid from finding the wrong centers of the drusen. This operation cannot avoid all wrong centers due to the presence of noise and pathologies. The wrong centers are further removed in the next steps of the method. In this step, a pixel is defined as the center of drusen or seed point if it is a peak in both x and y-axis direction as represented in FIG. 15 as "star" points. A pixel is defined as a local peak if it has higher or equal intensity than its neighbor pixels.

Potential Regions Finding Around Seed Points as Drusen.

Figure 16A:
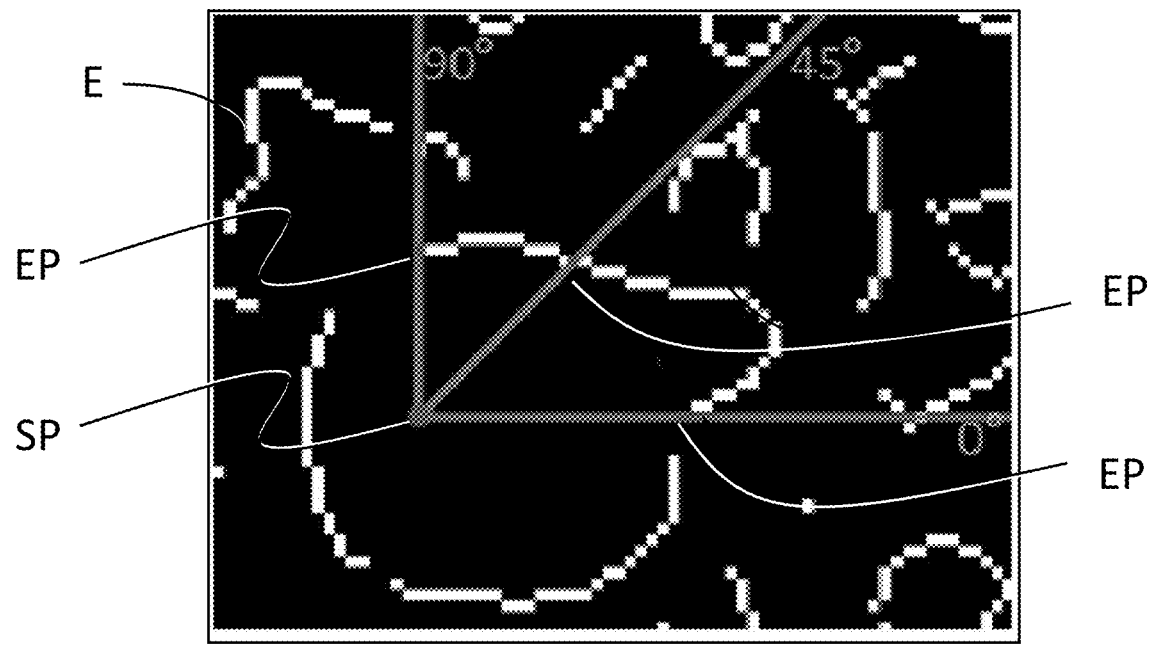
FIG. 16(a) is an image representing the drusen edge pixels E, seed point SP, the 0°, 45° and 90° angle lines from the seed point; and the nearest edge pixels EP along those lines in accordance with exemplary embodiments of the disclosed subject matter.
Figure 16B:
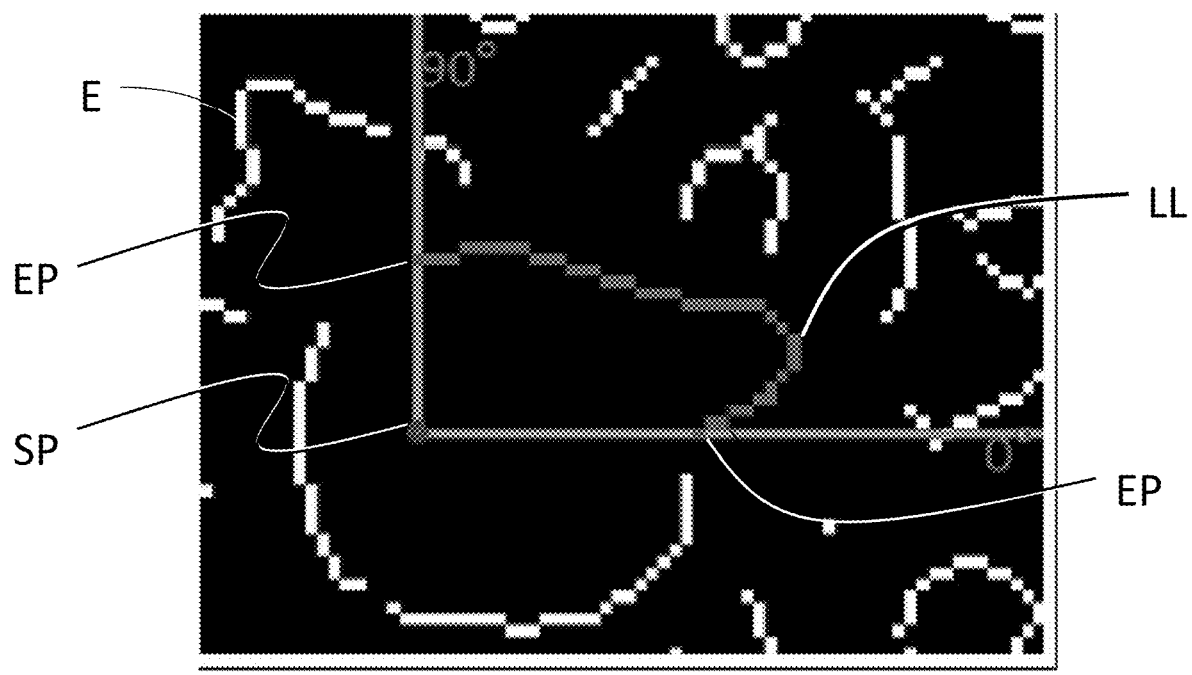
FIG. 16(b) is an image representing the longest line EL of the nearest edge pixels EP that cover 90-degree angle distance in accordance with exemplary embodiments of the disclosed subject matter.
Figure 17A:
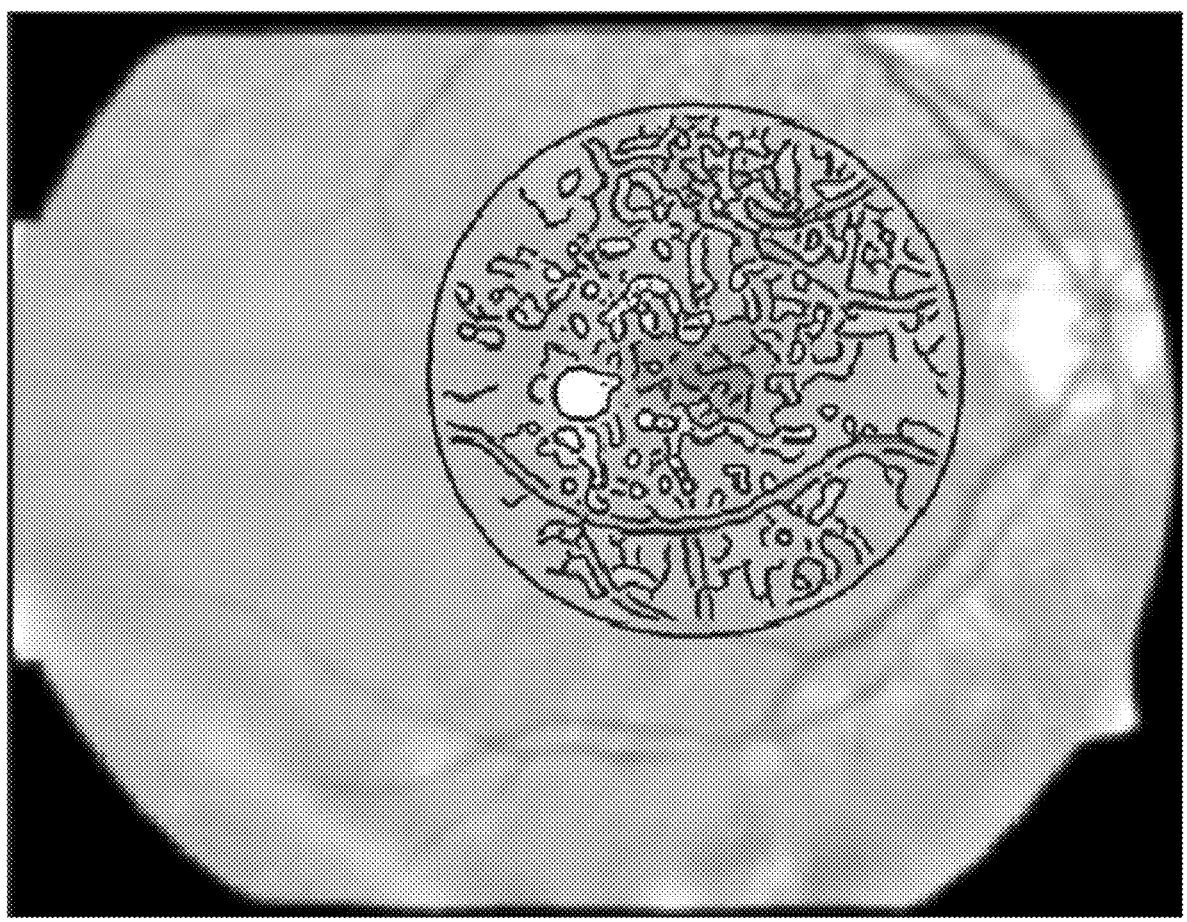
FIG. 17(a) is an image representing edge pixels using the Canny Edge Detection Algorithm in accordance with exemplary embodiments of the disclosed subject matter.
Figure 17B:
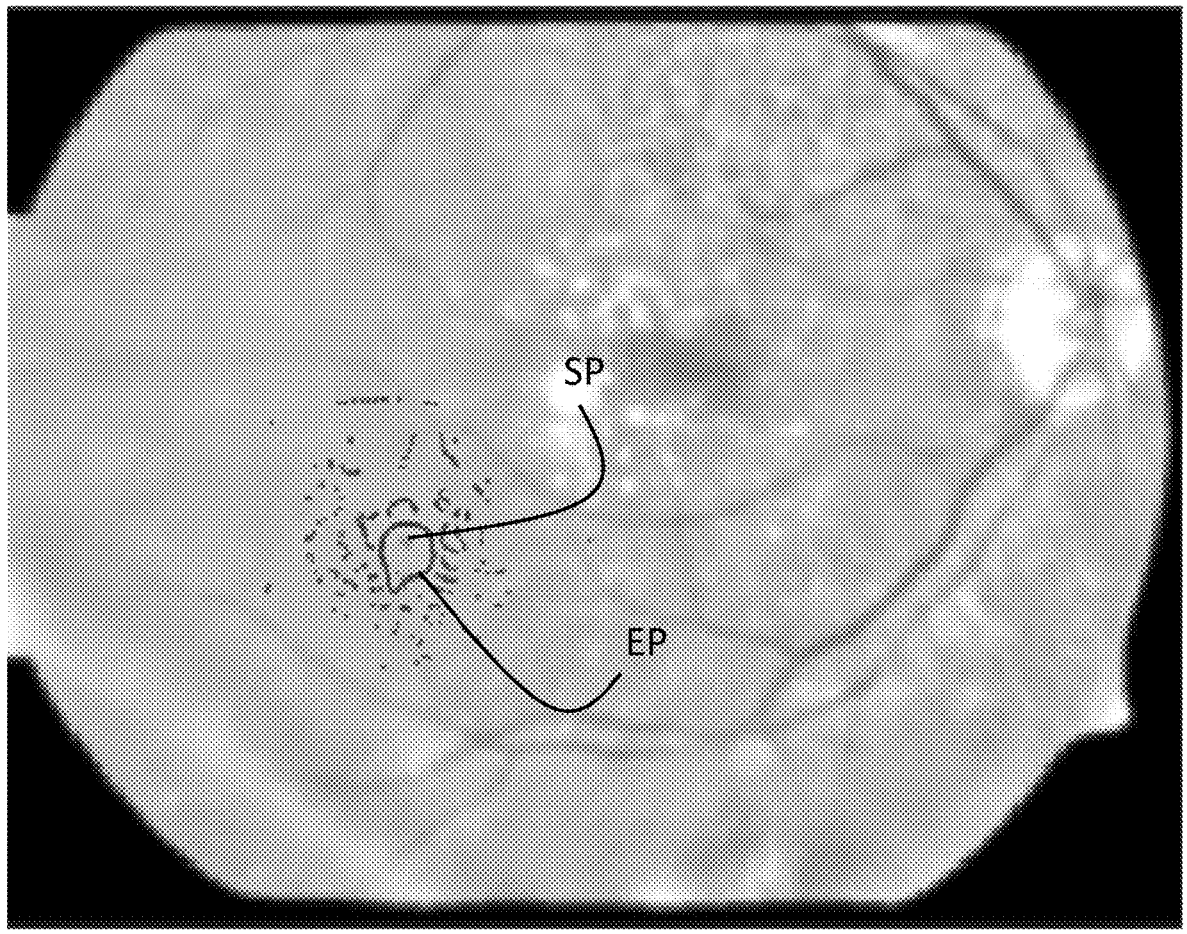
FIG. 17(b) is an image representing the nearest edge pixels EP from a seed point SP in accordance with exemplary embodiments of the disclosed subject matter.

Drusen are white pixels with an edge (border of the drusen) around it. The potential center of the drusen as a potential seed point has been described above in the previous step. At this step, the aim is to detect the edge around of each seed point that will determine as a potential region of drusen. The pseudo-code for potential region finding around seed points as drusen are provided in Algorithm 1. First, a Canny edge detection algorithm is applied for finding the edge in the image (see FIGS. 16(*a*) and 17(*a*)). After detecting edges E (white lines in FIGS. 16(*a*) and 16(*b*)), all edge pixels EP are located around each seed points SP. The nearest edge pixels EP in 0 to the 360-degree angle from each seed points SP (see FIG. 16(*a*)) are defined as edge pixels EP around the SP pixel as shown in FIG. 17(*b*). This operation finds corresponding border pixels of the seed point as well as some unwanted pixels. To keep only border pixels of the seed point, the shortest path algorithm is applied where each pixel is the graph node.

Figure 18A:
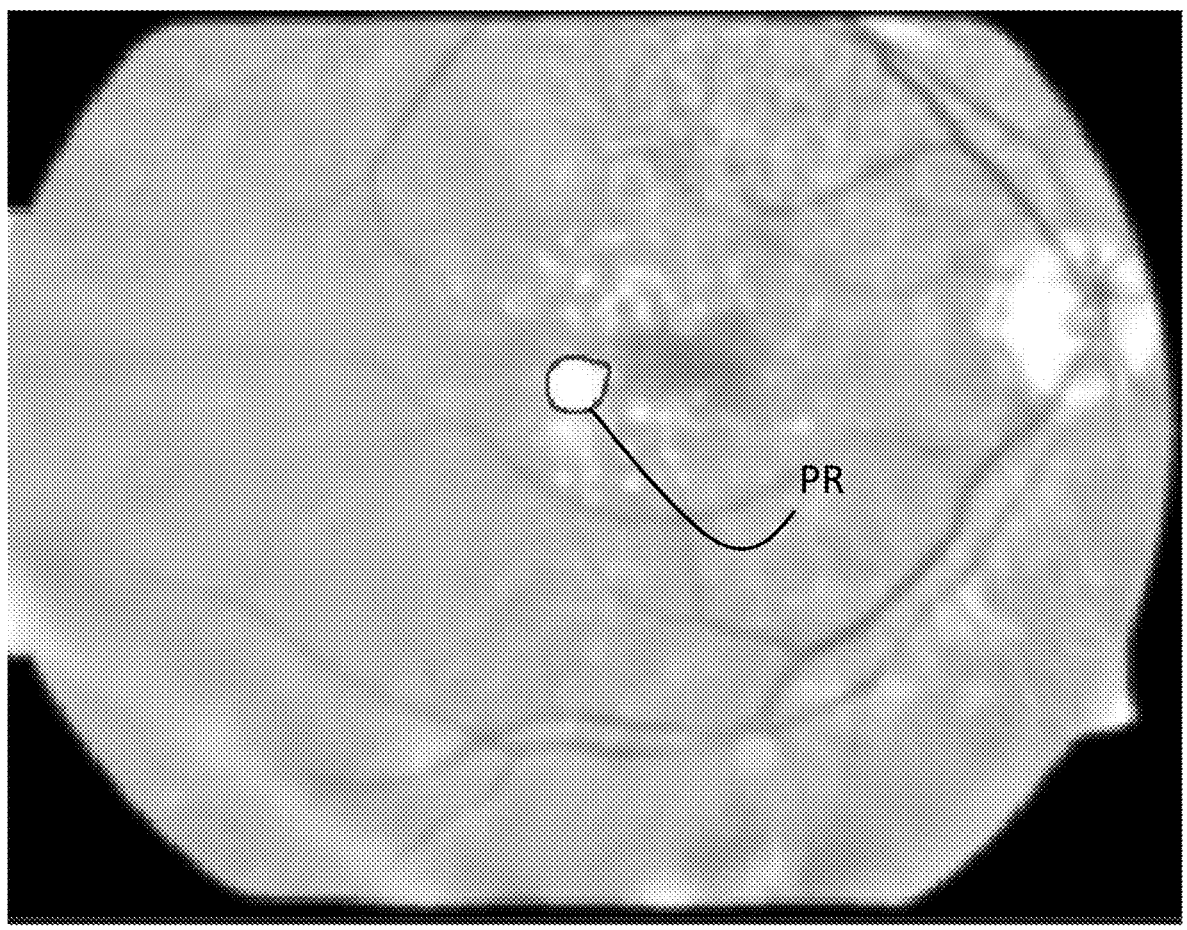
FIG. 18(a) is an image representing the potential region PR in accordance with exemplary embodiments of the disclosed subject matter.
Figure 18B:
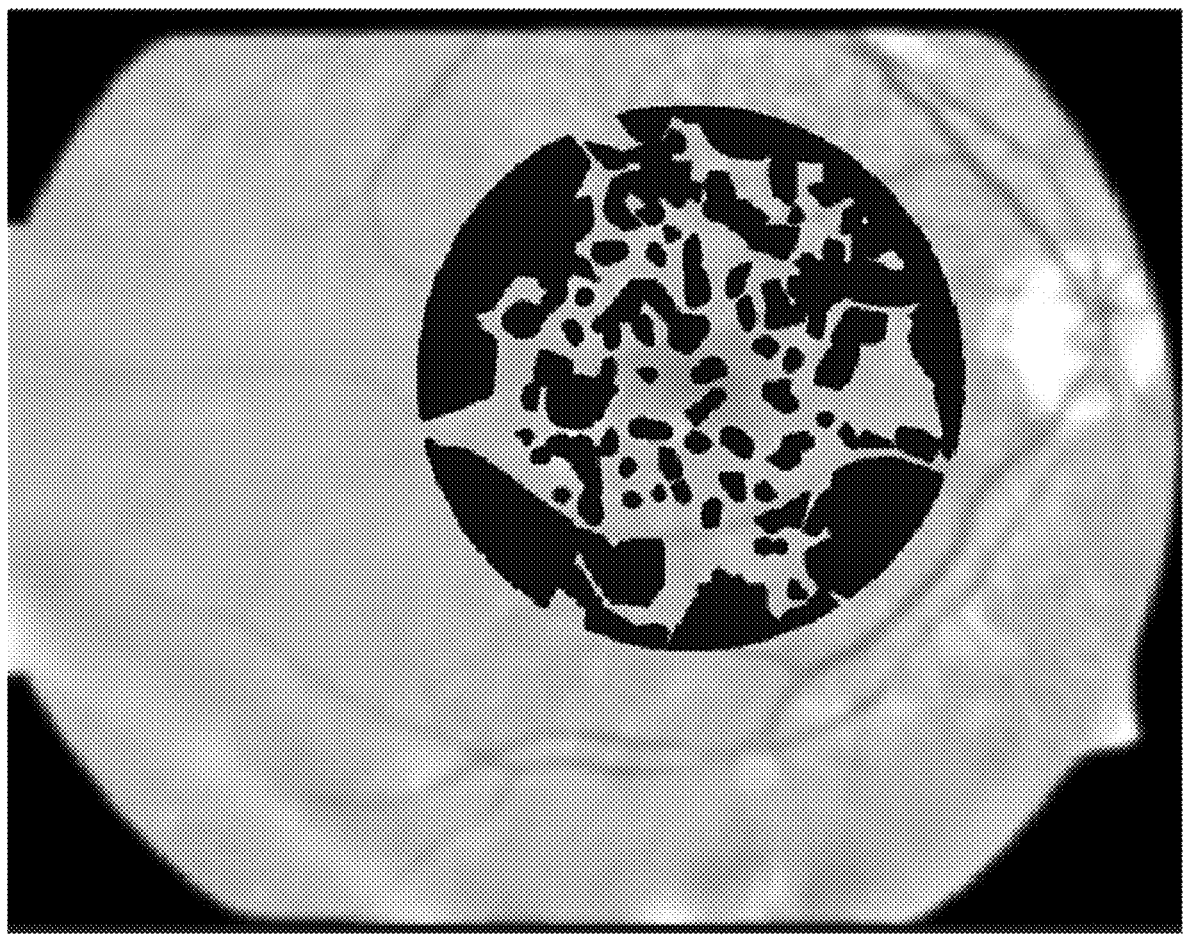
FIG. 18(b) is an image representing all potential region in the image in accordance with exemplary embodiments of the disclosed subject matter.

There are challenges to apply the shortest path algorithm, e.g., (1) which are the start and end nodes of the graph and (2) how to prevent non-border pixels from the shortest path. For the second challenge, the connected component of the graph is analyzed. If the Euclidean distance between the two pixels is less than two, then they are connected, and connected pixels form the connected component. If there is not a single longest line (connected component) which cover at least 90-degree angle distance (see FIG. 16(*b*)) for the seed point, then it is removed from the seed points. Otherwise, the end pixels of the longest line is defined as start and end nodes of the graph. The pixels associated with the longest line are removed from the graph so that the shortest path detect a different path for start and the end nodes that are the other side of border edge pixels of the drusen. The edge weight is the Euclidian distance from each pixel. Then the Dijkstra shortest path is applied to find the shortest path. If there is no shortest path, then this seed point is removed. Otherwise, the convex hull is applied on those edge pixels found from shortest path and the connected component. At this stage, the regions from all seed points are defined as a potential region of drusen (see FIG. 18(*b*)).

Defined Region as Drusen.

Figure 19:
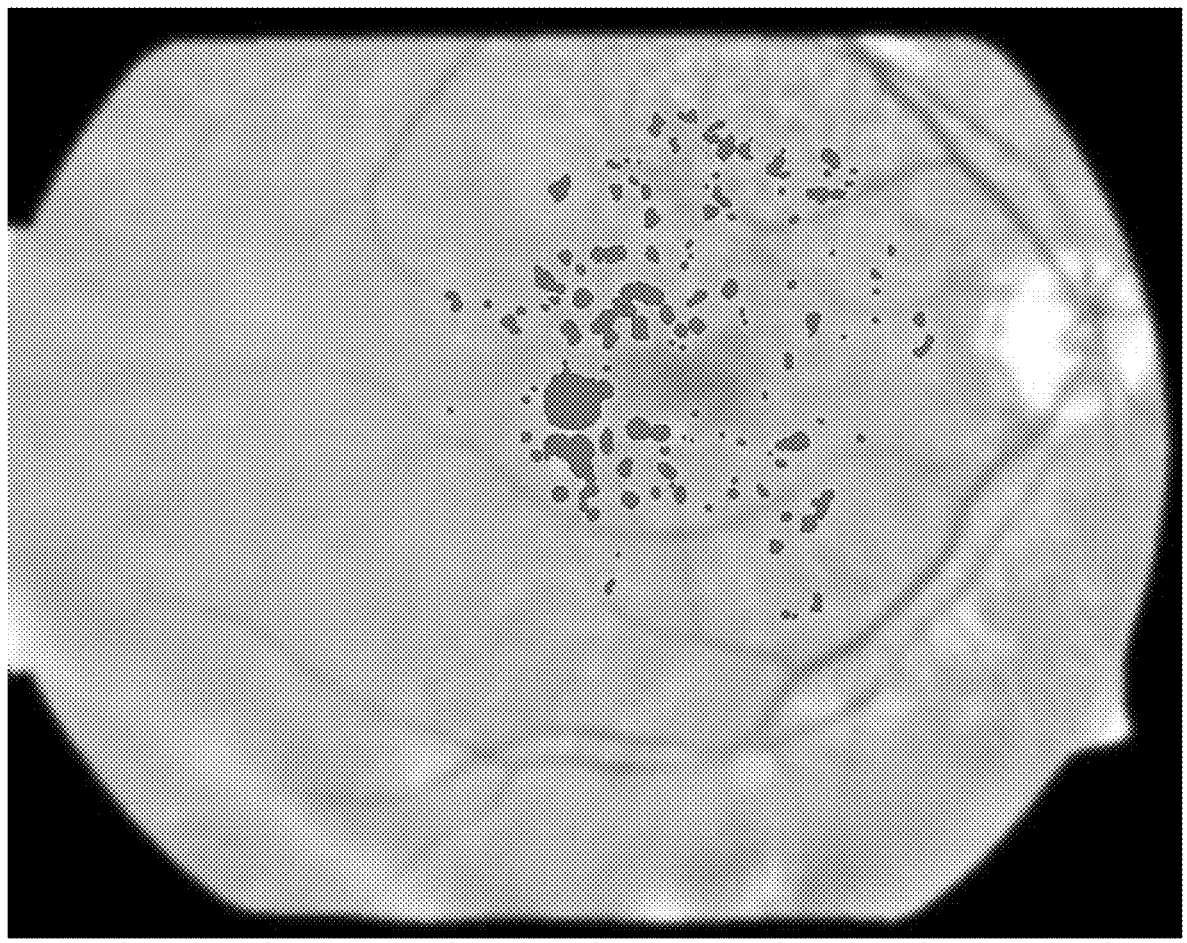
FIG. 19 is an image of drusen detected in accordance with exemplary embodiments of the disclosed subject matter.

In the edge detection process, all edges are detected including vessels and noises. As a result, potential regions could have a vessel(s) or other pathologies such as microaneurism. In this step of the algorithm, the wrong regions that are not drusen are eliminated. Since drusen are brighter than the background of the image, the ratio between potential regions and background are computed. The ratio greater than one is defined as drusen; otherwise remove as a wrongly-identified region. The value of background intensity is defined by the mean intensity plus two standard deviations of the intensity of the image, except the potential regions. Then the pixel intensity of the potential regions is divided by that background intensity. FIG. 19 shows an example of the drusen detected by the method.

```
Algorithm1: Detection of potential region of drusen from seed points

Potential RegionasDrusen
Input: seedPoints, img
Output: potentialRegion
   1. Detect edges of the image (img) using Canny Edge
   Detection Algorithm
   2. For each seed points in seedPoints
      a) Find nearest edge pixels in 0 to 360 degree angle
      b) Find the largest line of connected nearest edge pixels
      c) If the largest line not cover more than 0 to 90 degree angle Then
         Remove this seed point
      d) Else
         All nearest edge pixels form the graph nodes
         The end points of the longest line are the start and end nodes of
the
         graph
         Remove all edge pixels of the longest line from the nodes
         Compute edge weight using the Euclidian distance of pixels
(nodes)
            except the direct connection between the start and the end nodes.
            Apply Dijkstra shortest path algorithm
            If there are no shortest path found then
               Remove this seed point
            Else
               Apply convex hull on the edge pixels belonging to the shortest
               path and the largest line
               Add the region found from the Convex hull as
               potential region of
               drusen (potentialRegion).
```

Fusion of the Drusen and Other Features Computed from Machine Learning and Graph-based Method. The addition of the segmented images of machine learning 804 and graph-based method 806 is applied to obtain the final drusen and pathology segmented image. It is understood that either of the output images can be used without the fusion based on the quantified drusen information.

CF and RF image registration 410. CF and RF image are registered to map the macular area in RF image. For registration 410, elastic registration technique is used, relying on the vessel segmentation information. For this, average and median filtering and the image normalization technique described herein are applied. Then threshold technique is applied in the normalized image to produce a mask in the retinal area. Following this, Gabor filtering and canny edge filtering are applied. Then a threshold is applied to produce the vessel region and vessel edge information in the mask area. Finally, the vessel information is produced in the upper and lower boundary of the optic disc region following the one-third of the column in the left or right side of the image that is depending on the left or right eye. Vessel area more than 500 pixels and vessels which have higher length than width are kept. Finally, Euler Registration is applied to produce the registered image.

RPD Quantification 530. The segmentation model similar to that used in CF for machine learning based drusen segmentation is used to quantify RPD in RF imaging. For RF, the difference is that only the normalized intensity information is used along with texture. The focus is in the 3000 and 6000 µm radii of the macular area, where RPD usually occur. The characteristic RPD clustering is used in a single, well-defined region to differentiate them from drusen, which are usually randomly distributed in several small regions.

Deep Convolution Neural Network for AMD Screening 470. The deep convolution neural network 470, illustrated in FIG. 10, to train the AMD screening model 110 based on the individual's retinal image and socio-demographic data. Before inputting the images to the network, median filter and image normalization operation are applied. Gabor filtering is also used to feed the Gabor filter response to the network. Color fundus and red-free images are used along with patient's age, gender, smoking history, family history of AMD, BMI, exercise, expose to sunlight information to train the network.

Then the features are optimized by utilizing principal component analysis and then the selected features are used to train the dense layer of the network that is the fully connected neural network. The support vector machine is utilized with a non-linear regression model, random forest, conditional random field and Bayes classifier to find the individuals as AMD suspect.

For the screening model, Xception and Inception-Resnet-V2 network architectures are used to develop a model through ensemble methods. Xception and Inception-Resnet-V2 are considered state-of-the-art in image classification, as shown by their performance on the ImageNet dataset (1.2 million images with 1,000 classes). A stack of convolutional layers are used for feature extraction, dense layers (fully connected layers) are used for classification, and a final activation layer is used for output. These layers were optionally followed by Max-pooling, ReLU, dropout, and other layers for regularization and to prevent overfitting. A novel approach of training the network is used herein, combining transfer learning (by using weights from a pre-trained network, trained on ImageNet) and fine-tuning these weights by allowing all the layers to continue learning through a slow learning rate (usually it is done in the last few layers). This method drastically shortens the training time from a few days to a couple of hours.

The Inception module first performs the cross-channel correlations through a set of 1×1 correlations (e.g., a 1×1 filter). Then the output is separated into a few (usually 3 or 4) smaller spaces, which are then mapped through 3×3 or 5×5 correlations. In other words, there is a decoupling of spatial and cross-channel correlations. The separate, smaller spaces also allowed the network to learn relevant low-level and high-level features better by approximating optimal sparse structure. Inception modules drastically improved the network performance without adding computational complexity compared to similar deep networks.

Two classes are used for individuals: (1) normal/healthy individuals and (2) AMD suspect. The individuals who have no drusen or only a few hard drusen are considered as normal/healthy subjects. The individuals who have intermediate or soft drusen are considered as suspect (early or intermediate stage of AMD based on AREDS protocol). For developing the screening model, 128502 images were taken (out of nearly 149000 fundus images) for which grading information was available in the dataset. These images were graded on a scale of 1 to 4 (no AMD to Advanced AMD) based on their drusen characteristics and pigmentary abnormalities.

Results of the two models were combined to create the screening model, which takes the average of two probabilities given by the two models. This resulted in a classification accuracy of 95.3% for two classes, i.e., No AMD or Early AMD and Intermediate or Advanced AMD (AMD category '1 or 2' and '3 or 4').

AMD Prediction Model to Identify Individuals Who Are at Risk of Developing Late AMD in Near Future 120. As illustrated in FIG. 5, the automated AMD prediction model 120 can be based on cross-section and longitudinal patient data and color and/or red free Fundus imaging. Socio-demographic parameters 550 are used. The images are analyzed to quantify the drusen and AMD pathological information, e.g., to obtain the anatomical information and utilize the AMD categorical information obtained from deep convolution neural network and their weighted probabilistic score. Following this, the Principal Component Analysis (PCA) is applied to reduce the dimensionality and select the significant features related to the incident late AMD cases. Individuals who will develop late AMD in the near future are identified using these features and random forest classifier and support vector machine and their combined accuracy. Support vector machine and artificial neural network classifiers can also be used, in addition, these and combined the results based on decision stump.

A different feature-set is utilized depending on the individual's first visit or having a number of visits that are described as follows.

Prediction of AMD to identify the individuals at risk of developing late AMD based on patient cross-sectional data. For the first visit of an individual, the cross-sectional data is utilized. For this, the CF and RF images are analyzed, and information is obtained on the number of drusen that have more than 125 μm diameter, the area of drusen which have more than 125 μm diameter, the presence of Pseudo drusen and the total area of pseudo drusen, ten largest areas of drusen. Besides these anatomical features, the socio-demographic parameters and Deep Convolution Neural Network's (ConvNet's) features are used as the input to the dense layer for predicting an individual at risk of developing late AMD.

Prediction of AMD to identify the individuals at risk of developing late AMD based on longitudinal data. For the individual who has more than one visit, a number of additional features are added to the cross-sectional data based prediction model, e.g., the 10 largest areas of drusen from all available visits, the Maximum difference in drusen number in consecutive visits, the Maximum difference in drusen area in consecutive visits and total area change in the pseudodrusen. Also, other image based anatomical features are used, e.g., deep ConvNet based features, and socio-demographic features.

In the deep ConvNet model, following the feature optimization by PCA— the dense layer is utilized to perform the final classification. In some embodiments, the dense layer can be replaced with Random forest model, SVM, Bayesian Classifier and Conditional Random Field to predict the individual at risk of developing late AMD.

For AMD severity level categorization and fuzzy weighted score generation, the categorized AMD severity levels are: No AMD (severity level 1), Early AMD (severity level 2), Intermediate AMD (severity level 3) and Advanced AMD (severity level 4). Then the probability for each severity levels is generated based on the AREDS dataset by taking the incident of late AMD during later visits. The following are the steps for computing the fuzzy weighted score parameter (e.g., the iHS-AMD score) for late AMD.

The scoring scale is developed considering four pathologies, e.g., drusen area, and three pigment abnormalities (Increased Pigmentation, Depigmentation, and Geographic Atrophy). Deep learning-based classification system has been built for each of the four pathologies. Drusen Area is classified based on the size of the drusen. Pigment abnormalities are classified based on their size and location in the fundus image.

Combining the result of the four classifiers and using the same protocol as AREDS, nine probabilities for an image (for an eye) are obtained. The following methods in the document will be explained with "eye1" as an example. The nine probabilities of eye1 are referred to as: a, b, c, d, e, f, g, h, and i.

These are the probabilities that an image falls in the particular severity scale level 1-9. Further, the iHS-AMD score is obtained for the images from these probabilities using the four methods described below.

Method 1—First method is to use the scale level with the highest probability as the iHS-AMD score. For example, if 'd' is the highest probability, then the iHS-AMD score is 4.

TABLE 1 iHS-AMD score = Scale level for MAX(a, b, c, d, e, f, g, h, i)

Method 2—Here, the score is obtained using only the probabilities f, g, h and i. A custom fuzzification rule is applied, which is,

TABLE 2 iHS-AMD score = i + (0.8*h) + (0.6*g) + (0.4*f)

Method 3—In the third method, the resulting probabilities are fuzzified by applying the following rule, based on experimentation—Each probability is added to the weighted probabilities of its neighbors. Every probability is added with 80% of its immediate neighbors and 60% of its 2 step neighbors. See Table 3 for more details.

TABLE 3

| AMD Scale level | Probability | iHS-AMD score in Method 3 |
| --- | --- | --- |
| 1 | a | a + (0.8*b) + (0.6*c) |
| 2 | b | b + (0.8*a) + (0.8*c) + (0.6*d) |
| 3 | c | c + (0.6*a) + (0.8*b) + (0.8*d) + (0.6*e) |
| 4 | d | d + (0.6*b) + (0.8*c) + (0.8*e) + (0.6*f) |
| 5 | e | e + (0.6*c) + (0.8*d) + (0.8*f) + (0.6*g) |
| 6 | f | f + (0.6*d) + (0.8*e) + (0.8*g) + (0.6*h) |
| 7 | g | g + (0.6*e) + (0.8*f) + (0.8*h) + (0.6*i) |
| 8 | h | h + (0.6*f) + (0.8*g) + (0.8*i) |
| 9 | i | i + (0.6*g) + (0.8*h) |

In method 3, the iHS-AMD score is an array of 9 values as shown in the above table.

Method 4—The AMD severity scale used by AREDS is a nine-step severity scale on which the five-year risk of advanced AMD increased progressively from less than 1% in step 1 to about 50% in step 9. This information is used (as detailed in the table below) to develop the iHS-AMD score by multiplying each of the five-year risk probabilities with the severity scale probabilities (a,b,c, . . . ) that are obtained from our deep-learning based AMD severity classifier. The score from method 4 is also an array of nine values as shown in Table 4, below.

TABLE 4

| AMD Severity Scale | Average 5-year risk of Advanced AMD from AREDS study | iHS-AMD score in Method 4 |
| --- | --- | --- |
| 1 | 0.3% | a*(0.3%) |
| 2 | 0.6% | b*(0.6%) |
| 3 | 1.9% | c*(1.9%) |
| 4 | 4.9% | d*(4.9%) |
| 5 | 6.1% | e*(6.1%) |
| 6 | 13.9% | f*(13.9%) |
| 7 | 28.1% | g*(28.1%) |
| 8 | 47.4% | h*(47.4%) |
| 9 | 53.2% | i*(53.2%) |

Further, the score obtained from one method can be used independent of the scores from other methods or use any combination of them in developing the final model.

The two scores obtained from previous steps (AMD category and iHS-AMD score (Method 1 or 2 or 3 or 4 or all four)) are used to train the final model consisting of two classifiers along with the other parameters described earlier. First, a decision stump is used to train AMD category score against their label convert/non-convert. Second, a random forest classifier is used to train on iHS-AMD score values. The results from the two models are added to get the final prediction. In the alternative, SVM, ANN, RF, decision tree and decision stump can also be used together to produce a combined result.

A prediction score is computed based on the output of the model, and the ophthalmologist uses it for the final decision to take the necessary on treatment.

Dataset. For validation, the data from NAT-2 Dataset and AREDS dataset are utilized. The NAT-2 dataset has longitudinal data for three years for a total of 301 patients. Among them, 231 patients provide these features where 46 are converted to AMD and rest of the 185 patients are non-converted. The AREDS dataset has a total of 4613 images. Among them, 231 individuals are converted to late AMD in 10 years' time.

Results. The resulting model (when using the iHS-AMD score from all four Methods) achieved the sensitivity of 0.8879 and specificity of 0.7671 for the 2-year prediction model.

Figure 20:
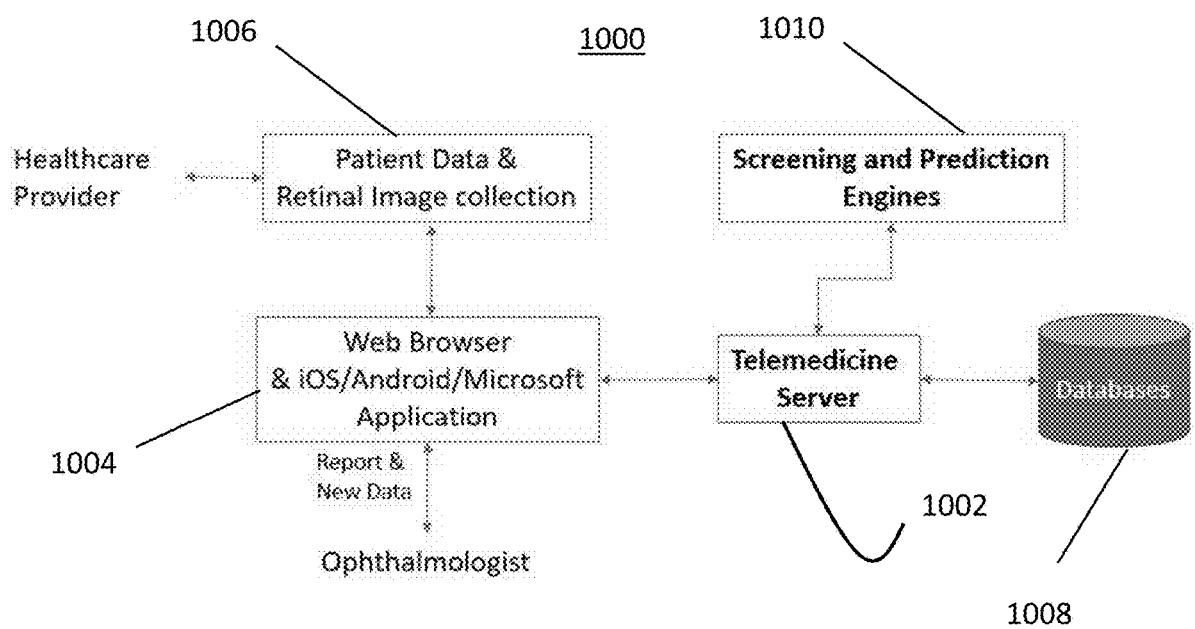
FIG. 20 is a diagram of the telemedicine platform in accordance with exemplary embodiments of the disclosed subject matter.

Telemedicine System for AMD screening. To make the image-based AMD screening system available widely to underserved areas, a telemedicine platform is utilized (FIG. 20). A telemedicine platform 1000 integrates the server 1002 (where the image analysis modules for AMD severity screening are situated) and local remote computer or mobile device(s) 1004 (for collecting patient data and images 1006). The remote device 1004, e.g., running a web browser and/or operating system such as iOs/Android/Microsoft, uploads images and data to the server 1002 to analyze and screen AMD automatically. In some embodiments, the data is de-identified according to well-known patient privacy protocols prior to uploading to the server 1002. In order to analyze the retinal data, the server can utilize data stored in a database 1008, which includes sociodemographic data, and can run the data screening and prediction engines 1010 as described above. In some embodiments, the images are resized for efficiency by splitting each image several times and merging it back on the server side. The image can also be cropped in the center area for efficient communication. The automatic analysis as described herein above is performed, and a report is sent from the server 1002 to the remote device 1004 with information including AMD stage, risk, and further recommendation to visit a nearby ophthalmologist. A re-identification and decryption module is provided at the remote device 1004, which is configured by machine-readable instructions to produce the report of individual's AMD stage with the image, individual's personal and pathological information. In some embodiments, the re-identification and decryption module is a processor at the remote device running software to perform the task of re-integrating the patient's identification information with the retinal data that was analyzed at the server 1002.

Automated Report Generation. A report is illustrated in FIG. 21, which can be generated in pdf version, and that includes patient personal information and retinal images. A software executable code is generated to take the input of retinal images with identified pathologies, quantified summary, the risk score for developing AMD and doctor's comments. The report can be directly viewed and can be received email or printout.

It will be appreciated that the methods and systems described above are set forth by way of example and not of limitation. Numerous variations, additions, omissions, and other modifications will be apparent to one of ordinary skill in the art. Thus, while particular embodiments have been shown and described, it will be apparent to those skilled in the art that various changes and modifications in form and details may be made therein without departing from the spirit and scope of this disclosure and are intended to form a part of the disclosure as defined by the following claims, which are to be interpreted in the broadest sense allowable by law.

What is claimed is:

1. A method for identifying individuals at risk of progression from intermediate stage AMD to late stage AMD comprising:
   receiving retinal image data and socio-demographic parameters; and
   performing AMD suspect screening comprising
   performing image data segmentation on the retinal image_to prepare a segmented image having prominent regions;
   performing elastic registration to the segmented image to prepare a registered image comprising the locations of an AMD pathology;
   generating a matrix from the registered image;
   training a deep convolution neural network with matrix data and socio-demographic parameters; and
   generating a fuzzy weighted score regarding risk of developing late AMD using the deep convolution neural network;
   wherein performing elastic registration to the segmented image to prepare a registered image comprising the locations of the AMD pathology comprises macular area mapping; and
   wherein macular area mapping comprises
   identification of the optic disc;
   identification of major vessel-segments about the optic disc boundary; and
   identification of the retinal raphe.

2. The method of claim 1, wherein receiving retinal image data comprises receiving color fundus (CF) and red free (RF) image data.

3. The method of claim 1, wherein receiving retinal image data comprises receiving color fundus (CF) image data.

4. The method of claim 1, wherein receiving retinal image data comprises receiving red free (RF) image data.

5. The method of claim 1, wherein macular area mapping further comprises detection of the macular center and selection of a 6000 micron diameter region about the macular center.

6. The method of claim 1, wherein generating the fuzzy weighted score comprises use of one or more of random forest, decision stump, support vector machine, or artificial neural network classifiers to predict the risk of progression from intermediate stage AMD to late stage AMD.

7. The method of claim 1, further comprising, prior to generating a matrix from the registered image, generating a normalized image including prominent features comprising performing one or more of median filtering, image normalization and Gabor filtering.

8. The method of claim 1, wherein training a deep convolution neural network with the matrix data and socio-demographic parameters comprises training the neural network to classify a pixel as RPD/ bright lesion or background;
mapping each of a plurality of RPD/pathology prominent regions;
analyzing the shape and size of one of the plurality of RPD/pathology prominent regions to determine if the region is soft or hard drusen.

9. The method of claim 1, further comprising:
if the AMD suspect screening provides a score indicative of progression from intermediate stage AMD to late stage AMD, performing an AMD incidence prediction comprising:
performing machine-learning on retinal image data comprising analyzing the shape of one of the prominent regions and analyzing the size of one of the prominent regions to distinguish drusen from background image data;
performing a graph-based method on the retinal image data for drusen quantification comprising normalizing the image data, detecting seed points based on local peak intensity, and detecting an edge around each seed point corresponding to the edge of the drusen;
merging the information from the machine-learning and graph-based methods to determine the drusen regions;
providing a prediction score;
if the prediction score indicates late stage AMD providing a treatment regimen; and
if the AMD suspect screening provides a score not indicative of progression from intermediate stage AMD to late stage AMD, recommending a repetition of the AMD suspect screening at a future time.

10. The method of claim 9, wherein detecting an edge around each seed point comprises
applying Dijkstra's shortest path algorithm and
analyzing color, intensity, and texture analysis with Gabor filter bank response.

11. A system for identifying individuals at risk of progression from intermediate stage AMD to late stage AMD, the system comprising a computer system having one or more processors comprising a server and a remote device said computer system configured by machine-readable instructions to:
receive at the server de-identified encrypted retinal image data from the remote device and socio-demographic parameters; and perform AMD suspect screening by performing the method of claim 1; and
transmit information from the server to the remote device regarding AMD stage, risk of progression from intermediate stage AMD to late stage AMD, and recommendation to visit an ophthalmologist immediately or at a certain time-frame.

12. The system of claim 11, wherein the information transmitted from the server to the remote device comprises an image that is cropped in the center area for a region of interest based on image center, and wherein the image is split into a plurality of parts for transmission from the server to the remote device.

13. The system of claim 11, further comprising:
a re-identification and decryption module at the remote device configured by machine-readable instructions to produce a report of individual's AMD stage with an image, and an individual's personal and pathological information.

14. The system of claim 11, wherein the retinal image data comprises color fundus (CF) and red-free (RF) image data.

15. The system of claim 11, wherein the retinal image data comprises color fundus (CF) image data.

16. The system of claim 11, wherein the retinal image data comprises red-free (RF) image data.

17. A method for identifying individuals at risk of progression from intermediate stage AMD to late stage AMD comprising:
receiving retinal image data and socio-demographic parameters; and
performing AMD suspect screening comprising
performing image data segmentation on the retinal image to prepare a segmented image having prominent regions;
performing elastic registration to the segmented image to prepare a registered image comprising the locations of an AMD pathology;
generating a matrix from the registered image;
training a deep convolution neural network with matrix data and socio-demographic parameters; and
generating a fuzzy weighted score regarding risk of developing late AMD using the deep convolution neural network;
wherein training a deep convolution neural network with the matrix data and socio-demographic parameters comprises
training the neural network to classify a pixel as RPD/ bright lesion or background;
mapping each of a plurality of RPD/pathology prominent regions; and
analyzing the shape and size of one of the plurality of RPD/pathology prominent regions to determine if the region is soft or hard drusen.

* * * * *